US012691210B2

(12) United States Patent
Chopra et al.

(10) Patent No.: US 12,691,210 B2
(45) Date of Patent: Jul. 28, 2026

(54) SYSTEMS AND METHODS FOR FAT HARVESTING

(71) Applicant: Chopra Gryskiewicz, LLC, Burnsville, MN (US)

(72) Inventors: Karan Chopra, Minneapolis, MN (US); Joseph M. Gryskiewicz, Edina, MN (US); Richard A. Thompson, II, Saint Louis Park, MN (US); Jason Scherer, Woodbury, MN (US); Mohamed Abdisalan Mohamed, Minneapolis, MN (US)

(73) Assignee: CHOPRA GRYSKIEWICZ, LLC, Burnsville, MN (US)

( * ) Notice: Subject to any disclaimer, the term of this patent is extended or adjusted under 35 U.S.C. 154(b) by 238 days.

(21) Appl. No.: 18/748,508

(22) Filed: Jun. 20, 2024

(65) Prior Publication Data

US 2024/0424185 A1     Dec. 26, 2024

Related U.S. Application Data

(60) Provisional application No. 63/522,528, filed on Jun. 22, 2023.

(51) Int. Cl.
*A61M 1/00* (2006.01)

(52) U.S. Cl.
CPC .............. *A61M 1/67* (2021.05); *A61M 1/815* (2021.05); *A61M 1/893* (2021.05); *A61M 2202/08* (2013.01)

(58) Field of Classification Search
CPC .. A61M 2205/7545; A61M 1/60; A61M 1/79; A61M 2205/3331; A61M 1/74; A61B 2217/005; A61B 2217/007; A61B 17/22; A61B 10/0283; A61B 2017/22079; A61F 13/05; C12M 45/02; C12M 47/04
See application file for complete search history.

(56) References Cited

U.S. PATENT DOCUMENTS

| | | | | |
|---|---|---|---|---|
| 9,248,384 B2 * | 2/2016 | Dominguez | ........... | B01D 17/08 |
| 9,358,327 B1 * | 6/2016 | Venturi | .................... | A61M 1/88 |
| 2012/0271254 A1 | 10/2012 | Schafer et al. | | |
| 2016/0208211 A1 * | 7/2016 | Cimino | .................. | A61L 27/00 |
| 2022/0325228 A1 | 10/2022 | Cimino et al. | | |
| 2022/0347374 A1 | 11/2022 | Chopra et al. | | |

FOREIGN PATENT DOCUMENTS

CN          209092303 U       7/2019

OTHER PUBLICATIONS

International Report on Patentability for PCT/US2024/034763, mailed Oct. 7, 2024, 7 pages.
International Search Report for PCT/US2024/034763, mailed Oct. 7, 2024, 5 pages.
Written Opinion of the ISA for PCT/US2024/034763, mailed Oct. 7, 2024, 6 pages.

* cited by examiner

*Primary Examiner* — Kai H Weng
(74) *Attorney, Agent, or Firm* — Husch Blackwell

(57) ABSTRACT

Some systems, devices and methods detailed herein provide fat harvesting from a body location, material screening, size selection, and extraction for fat preparation prior to reinjection into another body location.

20 Claims, 13 Drawing Sheets

SYSTEMS AND METHODS FOR FAT HARVESTING

CROSS REFERENCE TO RELATED APPLICATIONS

This application claims the benefit of U.S. Provisional Application Ser. No. 63/522,528, filed on Jun. 22, 2023, which is incorporated herein by reference in its entirety.

TECHNICAL FIELD

This disclosure describes systems, devices, and methods for fat harvesting, such as fat harvesting for transfer of fat from one location and reinjection into another location. Particular examples described herein provide an improved fat harvesting system that facilitates fat harvesting, material screening, size selection, and extraction for fat preparation prior to reinjection.

BACKGROUND

Fat harvesting can be utilized in cosmetic surgery procedures where fat cells are harvested from body locations having excess fat, such as, for example, the outer thighs and subsequently transferring/reinjecting the fats into other body locations such as, for example, the face, breasts, and buttocks. Fat transfer can be used to increase the size/volume of a body feature or alternatively, can be used to improve body contours, fill depressions or to revise the appearance of scars. Fat harvesting involves using autologous fat that can reduce a likelihood of allergic reactions that may be present with foreign substances, such as, implants and dermal fillers.

SUMMARY

This disclosure describes systems, devices, and methods for fat harvesting, for example, fat harvesting for transfer of fat from one location of a patient and reinjection into another location of the patient. In particular implementations, the systems, devices, and methods described herein can include a reservoir body that is connected to a vacuum source that facilitates the separation of fat cells from bodily fluids that include fat cells. Optionally, the separated fat cells can be collected and passed through an adjustable sizing screen before being extracted (e.g., by a syringe) for transfer/reinjection into another area of the patient. In some examples detailed below, the reservoir body can include one or more screens and one or more vacuum ports positioned in relation to the one or more screens that provides convenient adjustability for a user to tailor the extraction, screening, decanting, and separation of the fat cells from the bodily fluids (and/or other fluids). Additionally, the system can include a size-selector knob that provides the user with customized size selection for the fat cells that are extracted for reinjection.

Among other benefits, some systems and methods described herein can advantageously provide a more efficient and customizable approach to harvesting fat cells from a patient that efficiently separates the fat cells from the bodily fluid and facilitates a size selection of the separated fat cells for transfer/reinjection. Additionally, some embodiments described in more detail below can achieve an efficient, reliable solution that provides customization to a user to improve the quality and reliability of the harvested fat cells for reinjection based on an area of interest while also achieving efficient extraction of the fat cells and separation and disposal of the remaining bodily fluid.

Some embodiments described herein include a fat harvesting system. The fat harvesting system can include a reservoir body having an input fluid connector to receive bodily fluid including fat cells from a liposuction device so that the bodily fluid is deliverable into the reservoir body. The fat harvesting system may also include a first screen positioned gravitationally below the input fluid connector and extending across the reservoir body, the first screen having a first screen size. The fat harvesting system may optionally include a second screen positioned gravitationally below the first screen, the second screen having a tapered profile that slopes downwardly from an inner wall of the reservoir body to a collection chamber positioned along a midline of the reservoir body, the second screen having a second screen size that is smaller than the first screen size. Further, the fat harvesting system may include a vacuum control housing that includes a first vacuum port in communication with the reservoir body above the first screen and a second vacuum port in communication with the reservoir body below the second screen. The first vacuum port and the second vacuum ports can be positioned to remove a separated aqueous layer of the bodily fluid while a harvested fat layer including the fat cells remains in the reservoir body. The fat harvesting system may optionally include a wiper rotatably mounted within the reservoir body so as to rotate about an axis of the reservoir body in response to movement of an actuator external to the reservoir body. The wiper can have a set of blades disposed above the second screen. The fat harvesting system may include a conduit that extends from the collection chamber and is configured to connect to an extraction syringe to withdraw at least a portion of the fat cells from the collection chamber of the reservoir body. Optionally, the fat harvesting system includes an adjustable sizing screen positioned along the conduit and having a plurality of arcuate screen portions that are movable relative to the reservoir body so that said portion of the fat cells advance through a selected one of the arcuate screen portions before reaching the extraction syringe.

Such a system can include one or more of the following optional features. The fat harvesting system where the vacuum control housing includes a vacuum selector knob that is rotatable relative to the vacuum control housing, the vacuum selector knob is connected to a vacuum control housing valve that controls fluid communication through the vacuum control housing. The vacuum selector knob is rotatable to control the vacuum control housing valve to selectively provide fluid communication between the first vacuum port and a vacuum source, the second vacuum port and the vacuum source, both the first and second vacuum ports and the vacuum source, or neither vacuum port and the vacuum source. The fat harvesting system may include a fluid collection chamber gravitationally below the second screen. The fluid collection chamber is separated from the collection chamber. The second vacuum port is in fluid communication with the fluid collection chamber. Bodily fluid and fat cells can pass through the first screen and fat cells are prevented from passing through the second screen. The fat harvesting system the second screen may include a porous screen cover that prevents fat cells from passing through the second screen and permits bodily fluids to pass through the second screen. The set of blades have a blade profile that slopes downwardly to follow the tapered profile of the second screen. The set of blades includes a plurality of lateral portions that follow the tapered profile of the second screen and a plurality of vertical portions that extend vertically from the respective lateral ends of the plurality of lateral portions along the inner wall of the reservoir body. Responsive to movement of an actuator external to the reservoir body, the set of blades rotates to direct fat cells into the collection chamber. A first arcuate screen portion of the plurality of arcuate screen portions of the adjustable sizing screen has a first screen opening size, and a second arcuate screen portion of the plurality of arcuate screen portions of the adjustable sizing screen has a second screen opening size that is smaller than the first screen opening size. The fat harvesting system may include a size selector knob that is rotatable relative to the reservoir body so that the selected one of the arcuate screen portions is positioned to contact said portion of the fat cells. The adjustable sizing screen has a circular periphery and each arcuate screen portion is a 120-degree arcuate portion of the adjustable sizing screen. The fat harvesting system may include a wash introduction path in communication with the reservoir body to receive a wash fluid into the body reservoir so that the wash fluid contacts the harvested fat layer including the fat cells. A distal tip of the extraction syringe is releasable from the conduit so that said portion of the fat cells are transferable to a reinjection site. The fat harvesting system may include an additional extraction syringe that is releasably matable to the conduit to withdraw a second portion of the fat cells from the collection chamber of the reservoir body. The first screen and the wiper are removable from the reservoir housing. The system is a harvested fat protected system.

Some embodiments described herein include a fat harvesting method. The fat harvesting method includes receiving bodily fluid including fat cells in a reservoir body (optionally, from a liposuction device). The method may further include screening the bodily fluid by a first screen extending across the reservoir body, the first screen having a first screen size. The method may also include removing a portion of a waste fluid from the bodily fluid and the reservoir body by a first vacuum port positioned gravitationally above the first screen. The method can include capturing fat cells at a second screen gravitationally below the first screen, the second screen having a second screen size that is smaller than the first screen size. Optionally, the method may include removing a second portion of a waste fluid from the bodily fluid and the reservoir body by a second vacuum port positioned gravitationally below the second screen. The method can further include collecting fat cells in a collection chamber gravitationally below the second screen. The method can optionally include extracting fat cells through a selected screen portion of an adjustable sizing screen having a plurality of adjacent screen portions that are movable relative to the reservoir body and into an extraction syringe.

Such a method can include one or more of the following optional features and/or steps. The method may include rotating a set of blades positioned above the second screen to direct fat cells captured by the second screen towards a collection chamber. The method may include: introducing a wash fluid into the reservoir body; decanting the fat cells in the wash fluid for an interval of time; extracting the wash fluid; and extracting the fat cells into the extraction syringe. The first vacuum port and the second vacuum port are independently operable and operable together Some embodiments described herein include a system comprising a fat harvesting reservoir body having an input fluid connector to receive bodily fluid including fat cells. The system may also include a vacuum control housing that extends along an exterior of the fat harvesting reservoir body. The vacuum control housing optionally includes: a first vacuum port in communication with the reservoir body at a first location; a second vacuum port in communication with the reservoir body at a second location, the first vacuum port and the second vacuum ports are positioned to remove a separated aqueous layer of the bodily fluid from the fat harvesting reservoir body while a harvested fat layer including the fat cells remains in the fat harvesting reservoir body; and a vacuum selector knob that is rotatable relative to the vacuum control housing, the vacuum selector knob is connected to a vacuum control housing valve that controls fluid communication through the vacuum control housing.

Such a system can include one or more of the following optional features. The system where the vacuum selector knob is rotatable to control the vacuum control housing valve to selectively provide fluid communication between the first vacuum port and a vacuum source, the second vacuum port and the vacuum source, both the first and second vacuum ports and the vacuum source, or neither vacuum port and the vacuum source. The vacuum control housing is in fluid communication with a waste container and a vacuum source. The sizing screen has a sizing screen size and the pre-screen has a pre-screen size that is larger than a sizing screen size.

Some embodiments described herein include a fat harvesting system. The fat harvesting system may include a reservoir body having an input fluid connector to receive bodily fluid including fat cells. The fat harvesting system can also include a sizing screen positioned vertically lower than the input fluid connector. Further, the fat harvesting system may include a pre-screen that is vertically spaced apart from the sizing screen.

Some embodiments described herein include a fat harvesting system. The fat harvesting system includes a reservoir body having an upper portion configured to receive bodily fluid including fat cells, and a screen within the reservoir body and positioned vertically lower than the upper portion. The screen may optionally have a tapered profile that slopes downwardly from an inner wall of the reservoir body to a collection chamber positioned along a midline of the reservoir body. Further, the system may also include a wiper rotatably mounted within the reservoir body so as to rotate about an axis of the reservoir body in response to movement of an actuator external to the reservoir body. The wiper may optionally have a set of blades disposed above the second screen, the set of blades may include a plurality of lateral portions that have an arcuate profile and slope downwardly to follow the tapered profile of the second screen. The set of blades can be configured to rotate and direct fat cells into the collection chamber. A leading edge of the lateral portions may optionally create a concave surface.

Some embodiments described herein include a system. The system includes a reservoir body having an upper portion configured to receive bodily fluid including fat cells. Also, the system may include a first screen positioned vertically lower than the upper portion. The system may optionally include a second screen positioned vertically lower than the first screen. The system can include a collection chamber positioned along a midline of the reservoir body and vertically lower than the second screen, and a vacuum control housing that includes at least one vacuum port in communication with the reservoir body. The system can include a wiper rotatably mounted within the reservoir body and having a set of blades, and an adjustable sizing screen in fluid communication with the collection chamber.

Some embodiments described herein include a fat harvesting method. The fat harvesting method includes receiving bodily fluid including fat cells in a reservoir body; screening the bodily fluid by a first screen, and capturing fat cells at a second screen. The method may optionally include collecting fat cells in a collection chamber, extracting fat cells through and adjustable sizing screen and into an extraction syringe. The adjustable sizing screen may optionally include a plurality of differently sized screens that are moveable relative to the reservoir body.

Particular implementations can, in certain instances, realize one or more of the following advantages. First, some embodiments described herein provide a customizable and reliable approach to harvesting fat cells from a patient that efficiently separates the fat cells from the bodily fluid and facilitates a size selection of the separated fat cells for transfer/reinjection. Second, particular solutions described herein offer a readily sanitized, reusable system that is advantageously adjustable to harvest bodily fluids including fat cells from patients and screen the bodily fluids to separate the fat cells from the bodily fluids, select a size of the fat cells for reinjection, and extraction of increased volumes of fat cells of a selected size for reinjection into another area of the patient. Third, some embodiments described herein advantageously facilitate clearing of one or more screens to permit and/or increase fluid drainage through the one or more screens and increase the processing speed at which fat cells can be separated from the bodily fluid and extracted. Fourth, some embodiments described herein advantageously facilitate control of the suction throughout the system to facilitate customized user-selection and control of suction applied to different locations of the system and/or turned off to remove suction from the system. Fifth, some embodiments described herein prevent mixing of large particles with the harvested fat cells for extraction, thereby reducing and/or preventing clogging of the system. Sixth, some embodiments described herein facilitate the washing of the fat cells before the extraction of the fat cells from the system that advantageously facilitates rinsing, cleaning, and/or purifying the harvested fat cells before extraction of the fat cells.

Fourth, some embodiments described herein advantageously provide a "harvested fat protected" system. As used herein "harvested fat protected" means that the harvested fat that enters the reservoir body (e.g., from the liposuction tool) is not exposed to removable instruments/hand manipulation that can introduce contamination before the harvested fat is drawn into an extraction syringe for transfer and/or reinjection into the patient. In such embodiments, once the fat is outside of the patient's body, the harvested fat is closed within the system and not exposed to external contaminants (e.g., medical personnel, external stirrers or other medical tools. The harvested fat protected system can be implemented as a closed system that does not require the harvested fat to directly contact devices, users, or environments external to the reservoir body, conduits, and extraction syringe. The fat cells can be harvested from the patient, processed through the system and into the extraction syringe, and reinjected directly into the patient using the extraction syringe without retaining/contacting the extracted fat cells with other transfer devices. Particular implementations of the harvested fat protected system described below can advantageously facilitate atraumatic transfer of fat cells in a manner that reduces the likelihood of contamination and increases cleanliness and patent safety.

The details of one or more implementations are set forth in the accompanying drawings and the description below.

Other features, objects, and advantages will be apparent from the description and drawings, and from the claims.

DESCRIPTION OF DRAWINGS

Like reference symbols in the various drawings indicate like elements.

DETAILED DESCRIPTION

Figure 1:
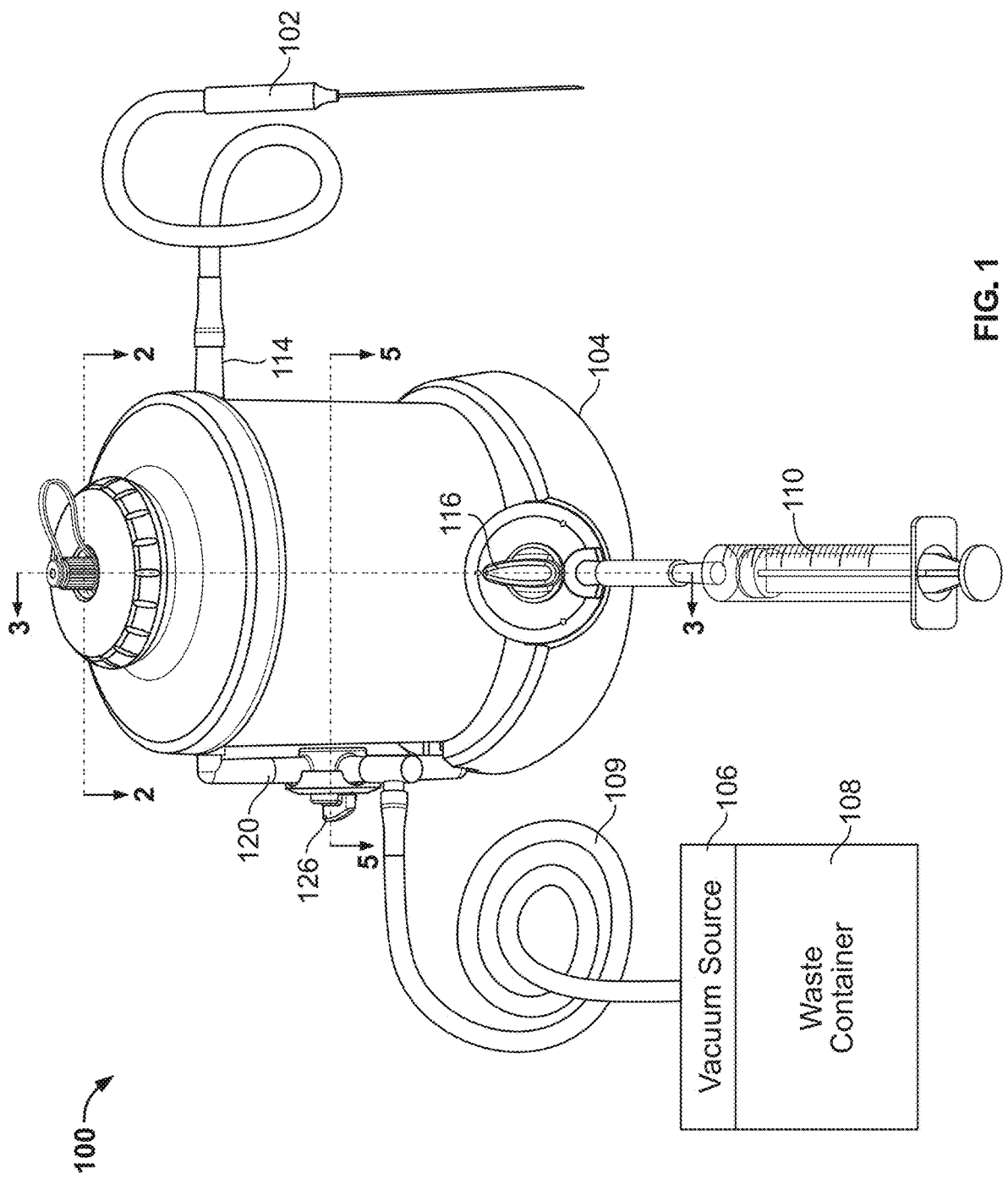
FIG. 1 shows a perspective view of an example system for fat harvesting and transfer, consistent with some embodiments of this disclosure.

Referring to FIG. 1, some embodiments of a fat harvester system 100 can be implemented to harvest fat from one location of a patient, to separate and wash the harvested fat, and to transfer at least some of the harvested fat (having a selected size) to another location of the patient. In this embodiment, the system 100 can include a liposuction tool 102, a reservoir body 104, a vacuum source 106, a waste container 108, and an extraction syringe 110. In the depicted embodiment, the liposuction tool 102 is in the form of a wand instrument configured to be inserted into a first area of the patient where excess fat cells can be harvested (e.g., the outer thighs, abdomen, buttocks). For example, the liposuction wand 102 can harvest bodily fluid including fat cells from the first area into the reservoir body 104. As described in more detail below, the reservoir body 104 is configured to screen and extract the fat cells from the bodily fluid, and at least some the extracted fat cells can be withdrawn from the reservoir body 104 into the extraction syringe 110 while the remaining material from the bodily fluid can be extracted (e.g., using the vacuum source 106) from the reservoir body 104 into the waste container 108. Optionally, the extraction syringe 110 can subsequently be detached from the reservoir body 104 to transfer/reinject the fat cells into a second area (e.g., the face, the cheeks, the lips, under the eyes, the breasts, and the buttocks). In some embodiments, the fat harvesting system 100 can be implemented in one or more medical procedures that include extracting, drawing, removing, or otherwise obtaining fat cells from a patient. For example, the fat harvesting system 100 can be utilized in plastic and reconstructive surgery, gastrointestinal and affiliated organ surgery, urological surgery, general surgery, bone or muscle surgery, gynecological surgery, thoracic surgery, minimally invasive surgery, among other procedures.

In this embodiment, the liposuction wand 102 can be connected to the reservoir body 104 at an input fluid connector 114, which is located at an upper portion of the reservoir body. In some embodiments, the liposuction wand 102 can include a needle and/or cannula that facilitates insertion into the patient. The liposuction wand 102 can be a powered liposuction device can expedite the harvesting of fat cells by vibrating the needle and/or cannula within the patient rapidly to break up the fat tissue and extract the fat tissue from the body and into the reservoir body 104.

The reservoir body 104 receives the bodily fluid including fat cells from the liposuction wand 102 at the input fluid connector 114, and as described in more detail below, the reservoir body 104 is equipped to isolate the fat cells from the harvested bodily fluid in a set of separation stages interior to the reservoir body 104. In some embodiments, the reservoir body 104 has a volume that can hold about 1000 to about 1500 cubic centimeters (cc), and preferably about 1200 cc of fluid (e.g., bodily fluid including fat cells). As described in more detail below, the reservoir body 104 includes a size selector knob 116 along its exterior that is rotatable relative to the reservoir body 104 to position a screen size between the reservoir body 104 and the extraction syringe 110, which can be used for selecting a particular size of the fat cells to be extracted from the reservoir body 104 and into the extraction syringe 110. The screening and extraction steps performed by the reservoir body 104 will be described in detail below (see e.g., FIGS. 2-14A-B).

In some optional embodiments, suction is applied through the reservoir body 104 for purposes of acting upon the bodily fluid while the bodily fluid is delivered into the reservoir body 104. The vacuum source 106 can apply suction to one or more vacuum ports in the reservoir body 104. As described in more detail below, the suction applied to the bodily fluid can facilitate the separation of the fat cells from the bodily fluid during the set of separation stages interior to the reservoir body 104. The separated fat cells can remain in the reservoir body 104 for selective withdrawal by the extraction syringe 110 while the remaining bodily fluid (after separation from the fat cells) is suctioned out of the reservoir body 104 and to the waste container 108.

Figure 2:
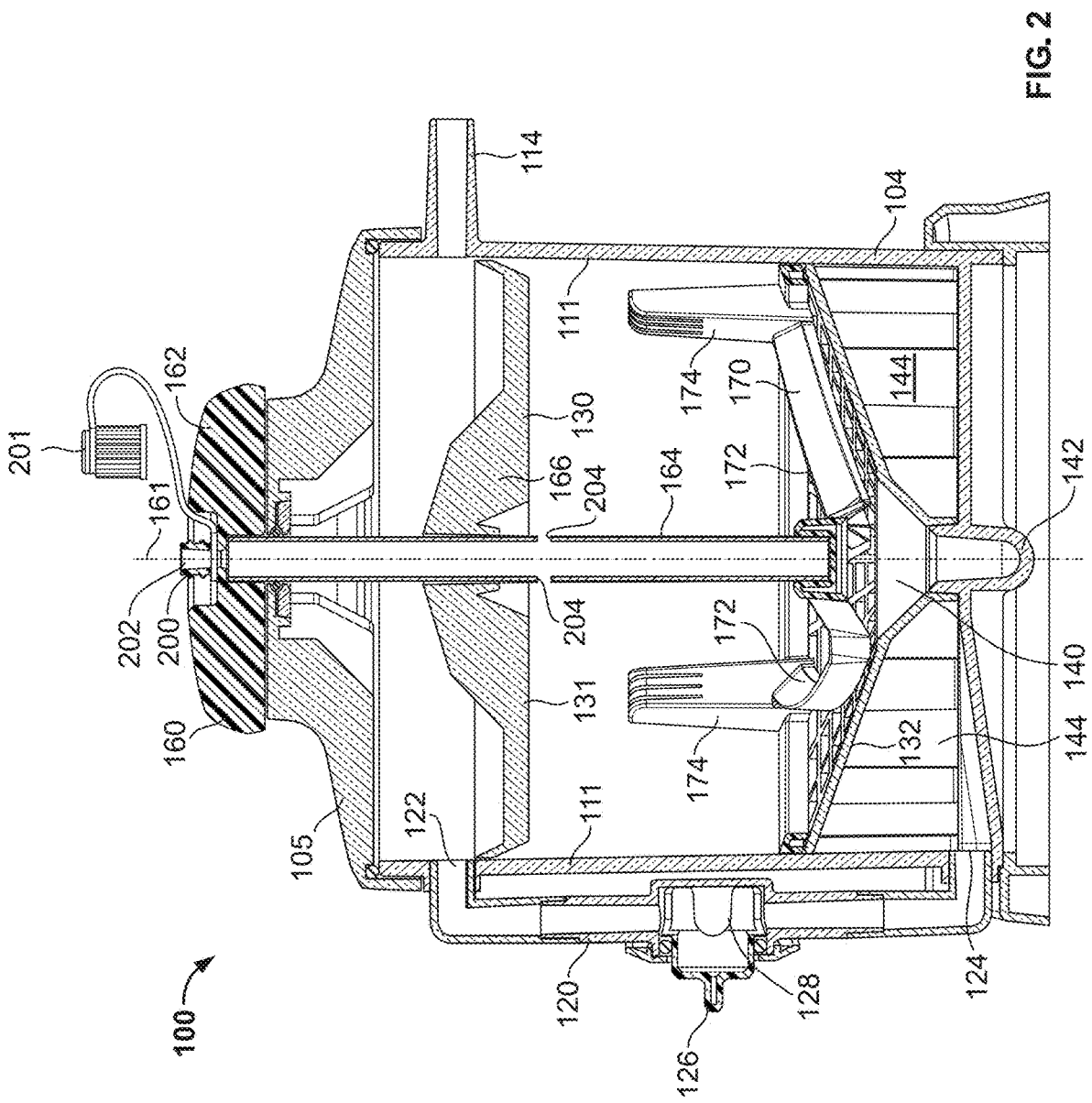
FIG. 2 shows a cross-sectional view of the fat harvesting system of FIG. 1 along the line 2-2.
Figure 3:
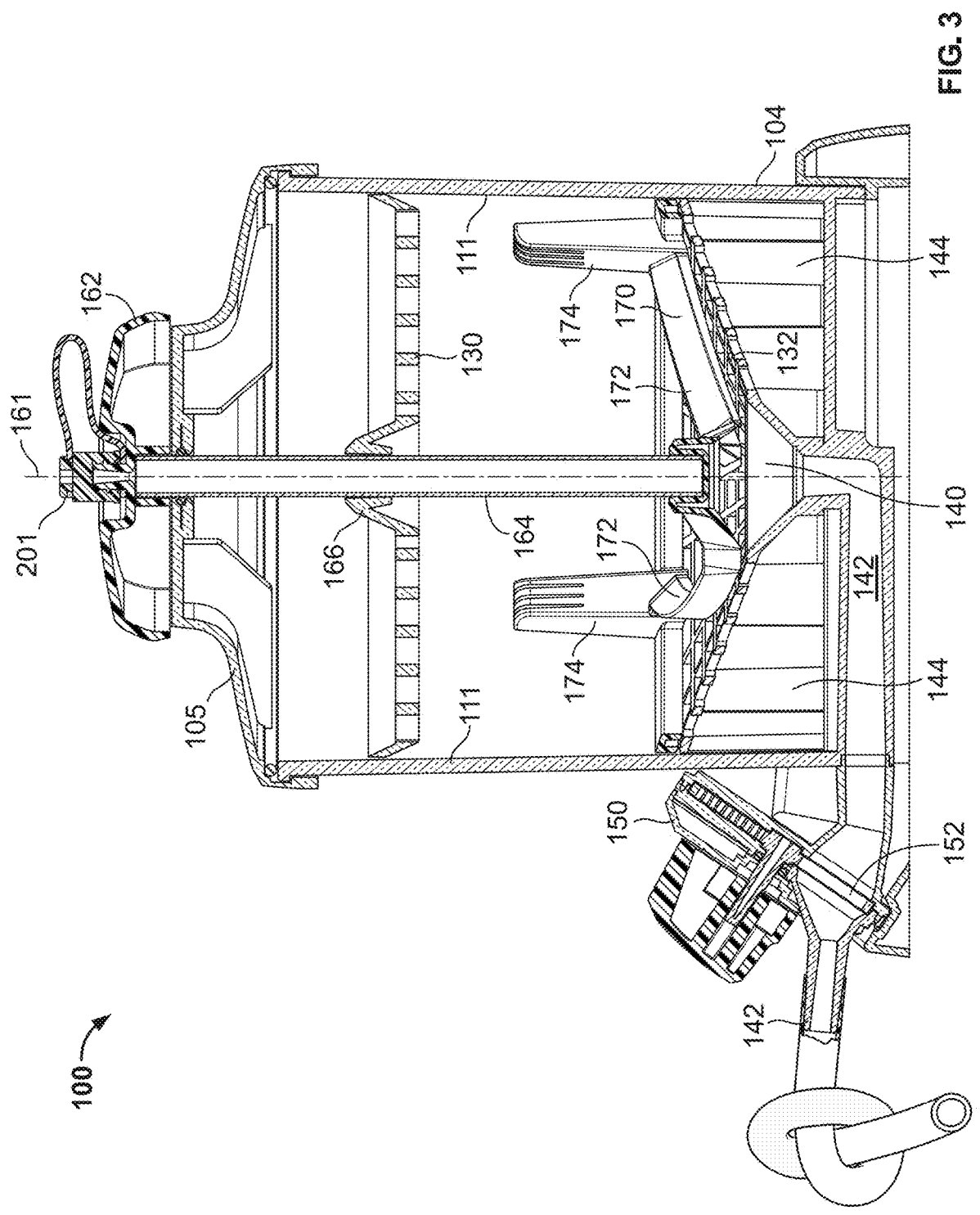
FIG. 3 shows a cross-sectional view of the fat harvesting system of FIG. 1 along the line 4-4
Figure 4:
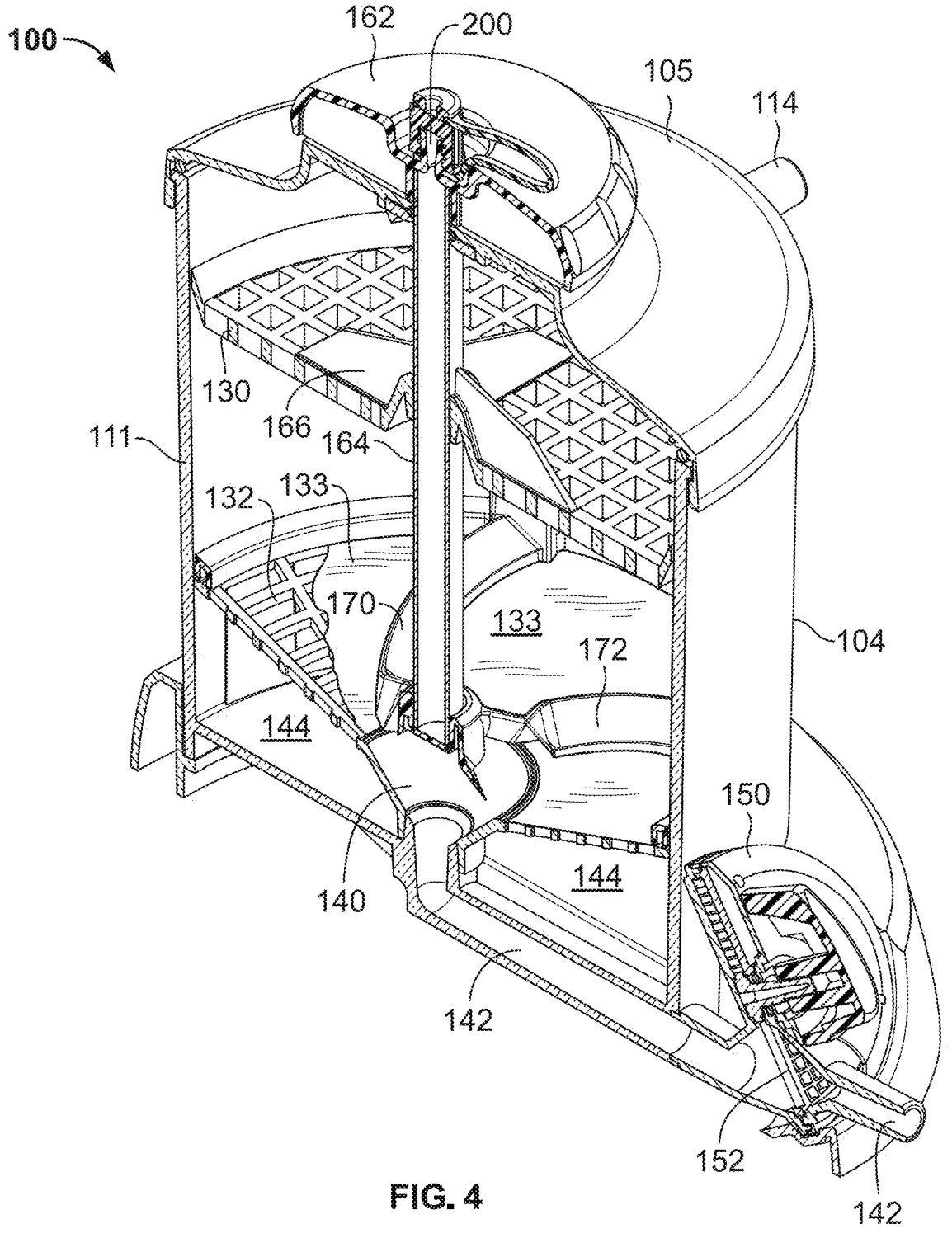
FIG. 4 shows a perspective view of the cross-sectional view of the fat harvesting system of FIG. 2.

Referring to FIGS. 2-4, the input fluid connector 114 can deliver bodily fluid from the liposuction wand 102 (FIG. 1) into the reservoir body 104 while the vacuum source 106 (FIG. 1) is applying suction to the reservoir body 104. The vacuum source 106 can be connected to the reservoir body 104 at a vacuum control housing 120 (e.g., via a conduit 109 that extends between the vacuum source 106 and the vacuum control housing 120, as depicted in FIG. 1). The vacuum control housing 120 includes a first vacuum port 122, a second vacuum port 124, a vacuum selector knob 126, and a vacuum control housing valve 128 that controls fluid communication through the vacuum control housing 120.

The first vacuum port 122 and the second vacuum port 124 can be positioned at opposing ends of the vacuum control housing 120. For example, the first vacuum port 122 is in communication with the reservoir body 104 above a first screen 130. The second vacuum port 124 is in communication with the reservoir body 104 below a second screen 132. In some embodiments, the first vacuum port 122 can be aligned with the input fluid connector 114. The first vacuum port 122 and the second vacuum port 124 are positioned to remove a separated aqueous layer of the bodily fluid while a harvested fat layer including the fat cells remains in the reservoir body 104. The separated aqueous layer of the bodily fluid can pass through either one of the first vacuum port 122 and the second vacuum port 124 or both the first vacuum port 122 and the second vacuum port 124, and can be suctioned through the vacuum control housing 120 and into the waste container 108 (e.g., via the conduit 109 that connects the waste container 108 to the vacuum control housing 120). In some embodiments, the separated aqueous layer can include a waste fluid that includes bodily fluids (e.g., blood) and other fluids such as washing fluids, saline solutions, or other fluids to be separated from the fat cells.

In some embodiments, the vacuum control housing 120 includes the vacuum selector knob 126. The vacuum selector knob 126 is rotatable relative to the vacuum control housing 120, and rotation of the vacuum selector knob 126 controls the position of the vacuum control housing valve 128 to control fluid communication through the vacuum control housing 120. In some embodiments, the vacuum selector knob 126 can include four positions that correspond to a respective four positions of the vacuum control housing valve 128 that can be a four-way valve. For example, the vacuum selector knob 126 can include an "off" position that positions the vacuum control housing valve 128 to block flow between the vacuum control housing 120 and the vacuum source 106. The vacuum selector knob 126 can include an "upper" position that positions the vacuum control housing valve 128 to provide fluid communication between the first vacuum port 122 and the vacuum source 106. The upper position blocks fluid communication between the second vacuum port 124 and the vacuum source 106. The vacuum selector knob 126 can include a "lower" position that positions the vacuum control housing valve 128 to provide fluid communication between the second vacuum port 124 and the vacuum source 106. The lower position blocks fluid communication between the first vacuum port 122 and the vacuum source 106. The vacuum selector knob 126 can include a "both" position that positions the vacuum control housing valve 128 in an open position that provides fluid communication between both the first vacuum port 122 and the vacuum source 106 and the second vacuum port 124 and the vacuum source 106.

Depending on the position of the vacuum selector knob 126 and the vacuum control housing valve 128, the vacuum source 106 can apply suction to different areas of the reservoir body 104 to remove waste fluid from the reservoir body 104. For example, in the upper position, the vacuum source 106 can apply suction in the reservoir body 104 above the first screen 130 to remove waste fluid from the reservoir body 104 above the first screen 130. In the lower position, the vacuum source 106 can apply suction below the second screen 132 to remove waste fluid from the reservoir body 104 below the second screen 132. In the "both" position, the vacuum source 106 can apply suction both above the first screen 130 and below the second screen 132 to remove waste fluid from the reservoir body 104 above the first screen 130 and below the second screen 132. The off position can remove the suction on the reservoir body 104 from the vacuum source 106.

The vacuum housing 120 and vacuum selector knob 126 facilitates control of suction acting above the first screen 130, below the second screen 132, or at both locations. Control of the suction throughout the reservoir body 104 facilitates customized user-selection and control of suction. For example, a user can select to retain bodily fluid and/or waste fluid within the reservoir body 104 along with the fat cells during the harvesting process. In some embodiments, retention of bodily fluid and/or waste fluid within the reservoir body 104 along with the fat cells during the harvesting process can improve fat cell survivability and facilitate a decanting process for the fat cells. The user can actuate the vacuum selector knob 126 to apply suction to the first vacuum port 122, the second vacuum port 124, or both the first vacuum port 122 and the second vacuum port 124 to drain the bodily fluid and/or waste fluid after the decanting process. Additionally, the vacuum selector knob 126 includes user-selectable both position that applies suction to both the first vacuum port 122 and the second vacuum port 124 to drain the bodily fluid and/or waste fluid while harvesting fat cells. The both position can be user-selected during the fat harvesting process and the decanting step can be omitted in some instances where the bodily fluid and/or waste fluid is removed during the procedure to process more volume through the system rapidly and efficiently. Also, the user can turn the vacuum off, which helps simplify the steps and not have to turn it off at the suction device.

Still referring to FIGS. 2-4, the first screen 130 can be positioned gravitationally below the input fluid connector 114 and the first vacuum port 122. The first screen 130 can extend across the reservoir body 104 between the interior walls 111 of the reservoir body 104, and the bottom surface 131 of the first screen 130 can have a horizontal or nearly horizontal profile that extends between the interior walls 111. The first screen 130 is spaced apart from the second screen 132 and a collection chamber 140 that collects the fat cells for extraction. The first screen 130 can include a grid of arms that are configured to collect large particles and prevent the large particles from dropping below the first screen 130. The first screen 130 can have a first screen size (e.g., size of the one or more openings in the grid of arms) that facilitates the collection of large particles while permitting fat cells and bodily fluid to pass through the first screen 130. In some embodiments, the large particles can include large fat globules, fibrous tissues, elongate tissue material, connective tissue, interstitial tissue, or other large particles that could clog the collection chamber 140.

The first screen 130 can collect the large particles vertically spaced apart from the second screen 132 and the collection chamber 140. The first screen 130 advantageously captures the large particles high above and away from the second screen 132 and prevents the large particles from entering the collection chamber 140. Capturing the large particles away from the second screen 132 prevents mixing of the large particles with the harvested fat cells for extraction. Additionally, the prevented mixing of the large particles with the harvested fat cells can reduce and/or prevent clogging of the second screen 132 and/or the adjustable sizing screen 152. Prevention and/or reduction of clogging at the second screen 132 and/or the adjustable sizing screen 152 facilitates rapid processing of the fat cells and facilitates improved quality of the harvested fat cells.

The fat cells and fluids that pass through the first screen 130 can be subsequently screened by the second screen 132. The second screen 132 can be positioned gravitationally below the first screen 130. The second screen 132 can extend across the reservoir body 104 between the interior walls 111 of the reservoir body 104, and the second screen 132 has a tapered profile that slopes downwardly from the interior walls 111 of the reservoir body 104 and into the collection chamber 140. In some embodiments, the second screen 132 can have a conical shape that defines the tapered profile where the outer most portions (e.g., adjacent to the interior walls 111) of the second screen 132 are positioned gravitationally higher than the inner most portions (e.g., adjacent to the collection chamber 140).

Still referring to FIGS. 2-4, the second screen 132 has a second screen size that is smaller than the first screen size. For example, the first screen 130 can have the first screen size to catch large particles while the second screen can have a smaller screen size than the first screen size so that the fat cells are captured by the second screen while the waste fluid (e.g., including bodily fluid and other fluids) passes through the second screen. In some embodiments, the second screen 132 can include a grid of arms that is covered by a porous screen cover 133. For example, FIG. 4 illustrates the porous screen cover 133 partially removed from view. While the porous screen cover 133 is partially removed from view in FIG. 4, and removed from view in the other figures, the porous screen cover 133 covers the second screen 132. For example, the porous screen cover 133 can extend across the entire second screen 132. The porous screen cover 133 can be supported by the grid of arms and can prevent fat cells from passing through the second screen 132 while permitting the waste fluid (e.g., including bodily fluid and other fluids) to pass through the second screen 132. In some examples, the porous screen cover 133 can be between a 100 and 300 micron nylon screen, between 150 and 250 micron nylon screen, between 175 and 225 micron nylon screen, or about 200 micron nylon screen.

The fat cells that are collected by the second screen 132 can be directed into the collection chamber 140. The collection chamber 140 can be positioned along a midline of the reservoir body 104 (the midline of the reservoir body 104 can be the axis 161 described below). The collection chamber 140 can have a tapered profile that has a generally conical shape that funnels the fat cells from the collection chamber 140 and into an extraction conduit 142. In some embodiments, the tapered profile of the collection chamber 140 can include a greater taper angle than a taper angle of the second screen 132. The collection chamber 140 can collect fat cells that are separated from the waste fluid, and the fat cells can be communicated through the collection chamber 140 and into the extraction conduit 142.

The collection chamber 140 can collect the fat cells that are captured at the second screen 132, and a fluid collection chamber 144 can collect the waste fluid that passes through the second screen 132. The fluid collection chamber 144 can be gravitationally below the second screen 132 so that the waste fluid can pass through the second screen 132 and into the fluid collection chamber 144. The fluid collection chamber 144 can circumferentially surround the collection chamber 140 and can extend from the collection chamber 140 to the inner walls 111 of the reservoir body 104 gravitationally below the second screen 132. The fluid collection chamber 144 is separated from the collection chamber 140 so that waste fluid in the fluid collection chamber 144 does not flow into the collection chamber 140 and into the extraction conduit 142. Similarly, the fat cells directed into the collection chamber 140 and the extraction conduit 142 are prevented from flowing into the fluid collection chamber 144. In some embodiments, the second vacuum port 124 is in fluid communication with the fluid collection chamber 144. The second vacuum port 124 can extract the waste fluid from the fluid collection chamber 144 and direct the waste fluid into the waste container 108.

Still referring to FIGS. 2-4, the fat cells directed from the collection chamber and into the extraction conduit 142 can pass through an adjustable sizing assembly 150 positioned between the collection chamber 140 and the extraction syringe 110. For example, the extraction conduit 142 can extend below the fluid collection chamber 144 and to the adjustable sizing assembly. The adjustable sizing assembly 150 positions an adjustable sizing screen 152 along the extraction conduit 142. The adjustable sizing screen 152 has a plurality of arcuate screen portions that are movable relative to the reservoir body so that the fat cells in the extraction conduit 142 advance through a selected one of the arcuate screen portions before reaching the extraction syringe. The adjustable sizing assembly 150 including the adjustable sizing screen 152 will be described in detail below (see e.g., FIGS. 8 and 9). The extraction conduit 142 can continue beyond the adjustable sizing screen 152 and can be configured to connect to the extraction syringe 110 to withdraw at least a portion of the fat cells from the collection chamber 140 of the reservoir body 104.

In some embodiments, the system 100 includes a wiper assembly 160 that is mounted within the reservoir body 104. The wiper assembly 160 includes an actuator 162 that is connected to a shaft 164 that extends downwardly into the reservoir body 104 from the actuator 162. The shaft 164 extends to a first set of blades 166 positioned at the first screen 130. In some embodiments, the first set of blades 166 and the first screen 130 are integrated with each other and are connected to the shaft 164. The first set of blades 166 extend above a top surface of the first screen 130.

The wiper assembly 160 includes a second set of blades 170 connected to the shaft 164 and disposed above the second screen 132. The second set of blades 170 include a blade profile that slopes downwardly to follow the tapered profile of the second screen 132. The second set of blades 170 includes a plurality of lateral portions 172 that follow the tapered profile of the second screen 132. The second set of blades 170 include a plurality of vertical portions 174 that extend vertically from the respective lateral ends of the plurality of lateral portions 172 along the inner wall 111 of the reservoir body 104. The second set of blades 166 will be described in detail below (see e.g., FIGS. 5-7).

The wiper assembly 160 can rotate about the axis 161 of the reservoir body 104. For example, in response to movement (e.g., rotation) of the actuator 162 external to the reservoir body 104, the wiper assembly 160 can rotate. The wiper assembly 160 is free to rotate clockwise and counterclockwise, and rotation of the actuator 162 imparts rotation to the shaft 164 that transfers the rotation to the first set of blades 166 and the second set of blades 170. In some embodiments, the first set of blades 166 and the first screen 130 both rotate together responsive to rotation of the shaft 164.

The wiper assembly 160 can be rotated to facilitate processing of the bodily fluid, waste fluid, and fat cells within the reservoir body 104. For example, the rotation of the first set of blades 166 and the first screen 130 can agitate large particles captured by the first screen 130 and facilitate movement of the bodily fluid and fat cells through the first screen 130. Rotation of the second set of blades 170 with respect to the second screen 132 can agitate tissues and particles captured at the second screen 132. Clockwise rotation of the second set of blades 170 can guide the fat cells captures at the second screen 132 into the collection chamber 140.

Still referring to FIGS. 2-4, in some embodiments, the wiper assembly 160 incudes a wash introduction path 200 in communication with the reservoir body 104. The wiper assembly 160 incudes a wash inlet 202 that can be capped when the wash introduction path 200 is not in use to maintain suction in the reservoir body 104. The wash introduction path 200 is configured to receive a wash fluid (e.g., from an external wash fluid source) and introduce the wash fluid into the reservoir body 104 through the wash openings 204. For example, the wash fluid can be introduced though the wash openings 204 to contact the harvested fat layer including the fat cells. The wash openings 204 can extend through the shaft 164 and can be positioned below the first screen 130 (e.g., just below the first screen 130 in the depicted embodiment). The wash openings 204 can direct the wash fluid to sprays evenly over the top layer of the harvested fat (e.g., collected at the second screen 132 or floating on top of the bodily fluid and/or waste fluid in the reservoir body 104. The spraying of wash fluid through the wash openings 204 facilitates a flushing of a top oil layer (e.g., on top of the layer of fat cells) for better cleaning of the fat cells. In some embodiments, the wash fluid can include a saline solution that is utilized to rinse, clean, and/or purify the harvested fat cells before extraction of the fat cells.

In some embodiments, the wash fluid can be introduced into the reservoir body 104 through the input fluid connector 114 and/or through the wash inlet 202. In some implementations, the user does not have to disconnect the liposuction tool 102 from the input fluid connector 114 to introduce the wash fluid. The user can remove the cap 201 at the wash inlet 202, and the user can connect a wash fluid source (e.g., IV bag of saline solution, lactated ringers) to the wash inlet 202 via a luer fitting at the wash inlet 202. In some embodiments, a user can connect a wash fluid source to the wash inlet 202 during the harvesting of fat cells to facilitate simultaneous washing and harvesting to further reduce the overall processing time and continuously flush the contents. In some embodiments, the wash fluid can be introduced during a decanting process where the fat cells are held in the reservoir body 104 for an interval of time. The decanting process will be described in further detail below (see e.g., FIGS. 12-14B). In some embodiments, the wiper assembly 160 is removable from the reservoir body 104. For example, the wiper assembly 160 can be releasably attached to the reservoir body 104 and can be removed for cleaning, inspection, or replacement. When the wiper assembly 160 is removed, the actuator 162, the shaft 164, the first screen 130, the first set of blades 166, and the second set of blades 170 can be removed from the reservoir body 104. In some embodiments, a cover 105 of the reservoir body 104 can be twisted and removed from the reservoir body 104. The cover 105 can be connected to the wiper assembly 160, and removal of the cover 105 can facilitate removal of the first screen 130 from the reservoir body 104. Removal of the cover 105 and the wiper assembly 160 (e.g., including the first screen 130) facilitates direct access to the harvested fat in the reservoir body 104 for removal. The removable cover and wiper assembly facilitates additional flexibility to extract the processed fat into other devices such as directly into the barrel of a syringe or other container, bypassing the sizing system and therefore allowing the less traumatic transfer. Removal of the cover 105 and opening the reservoir body 104 can remove the system 100 from a harvested fat protected state.

Figure 5:
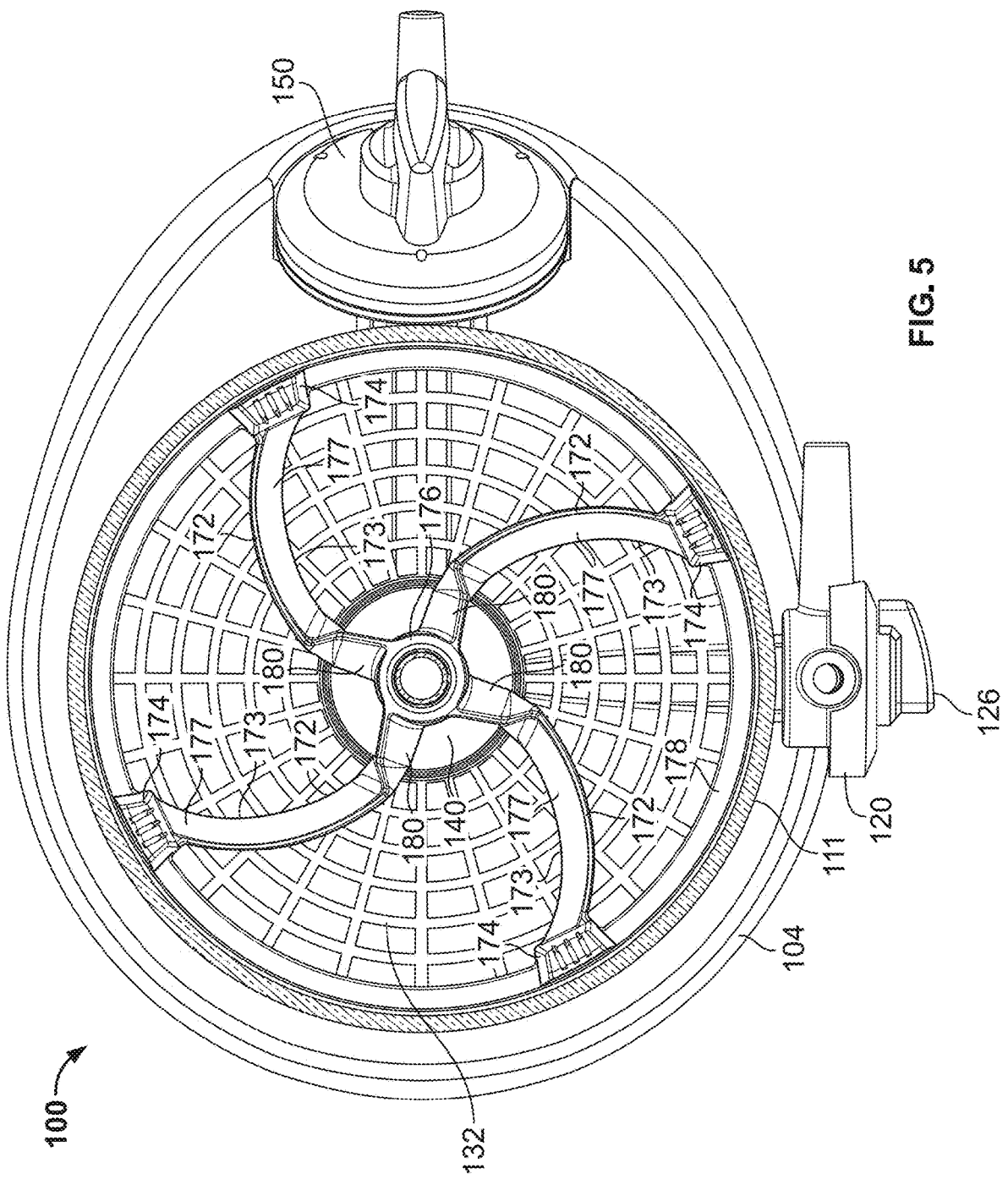
FIG. 5 shows a cross-sectional view of the fat harvesting system of FIG. 1 along the line 5-5.
Figure 6A:
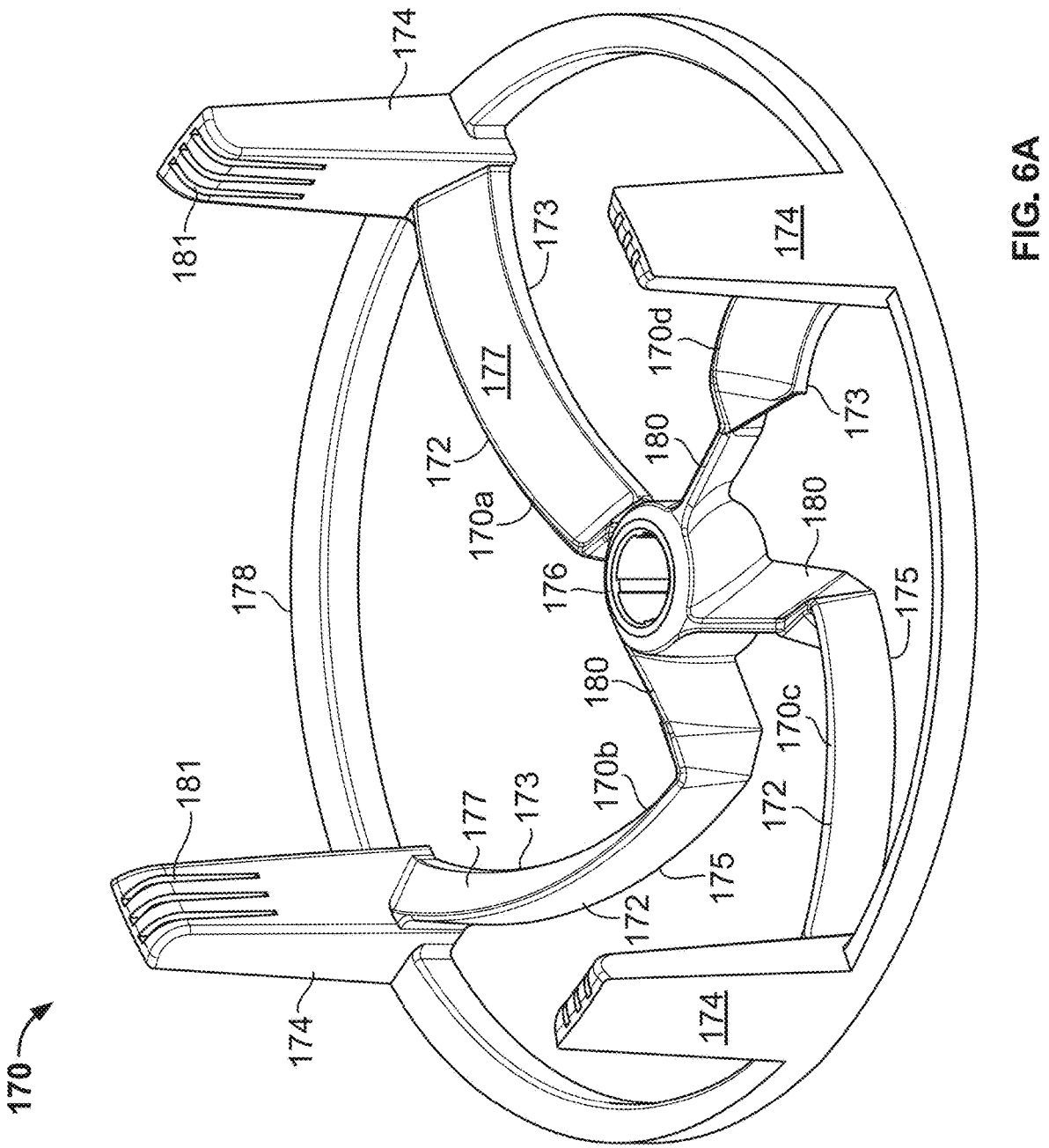
FIG. 6A shows a perspective view of a blade assembly removed from the system for fat harvesting, consistent with some embodiments of this disclosure.
Figure 6B:
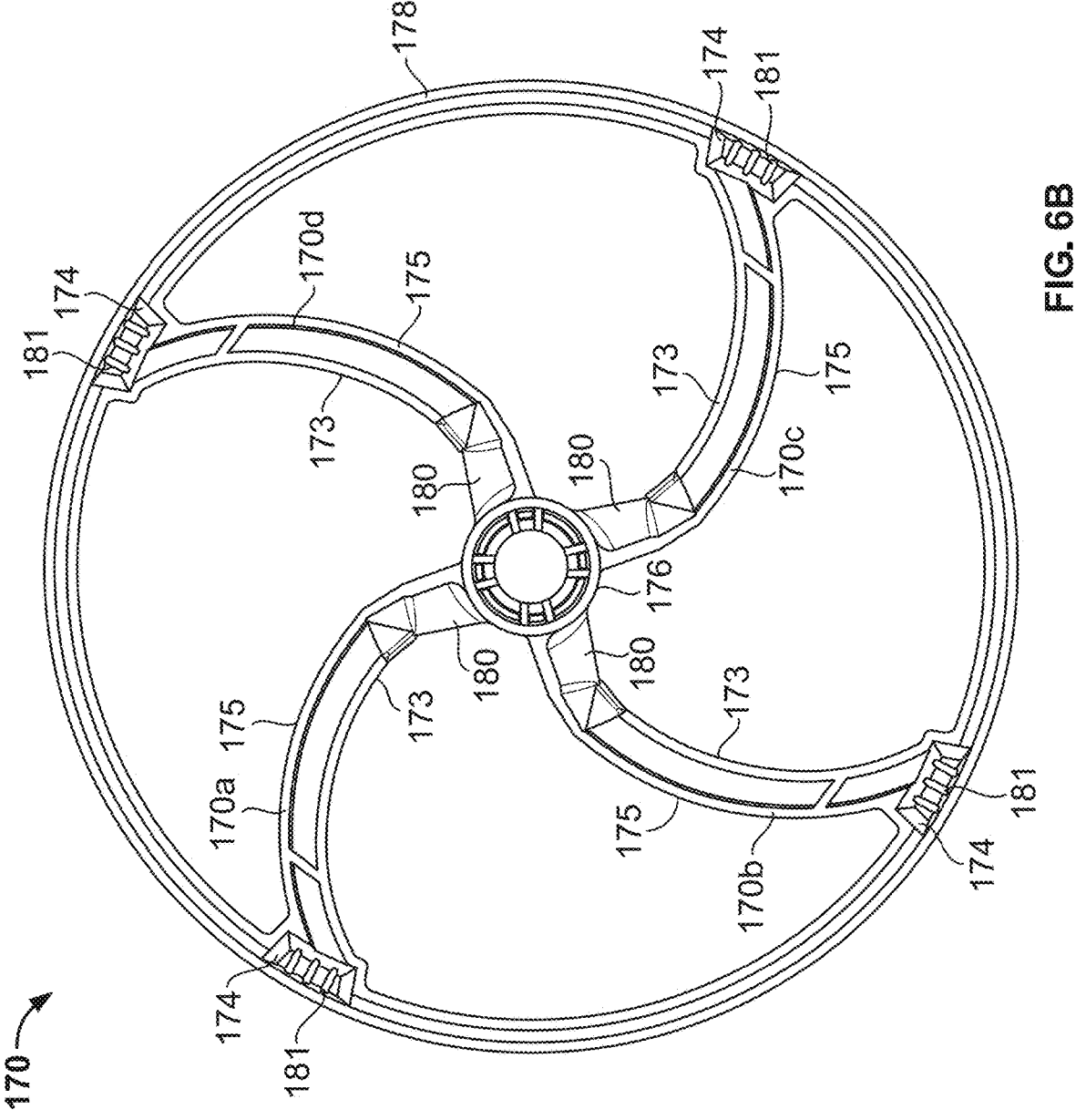
FIG. 6B is a bottom view of the blade assembly of FIG. 6A.
Figure 7:
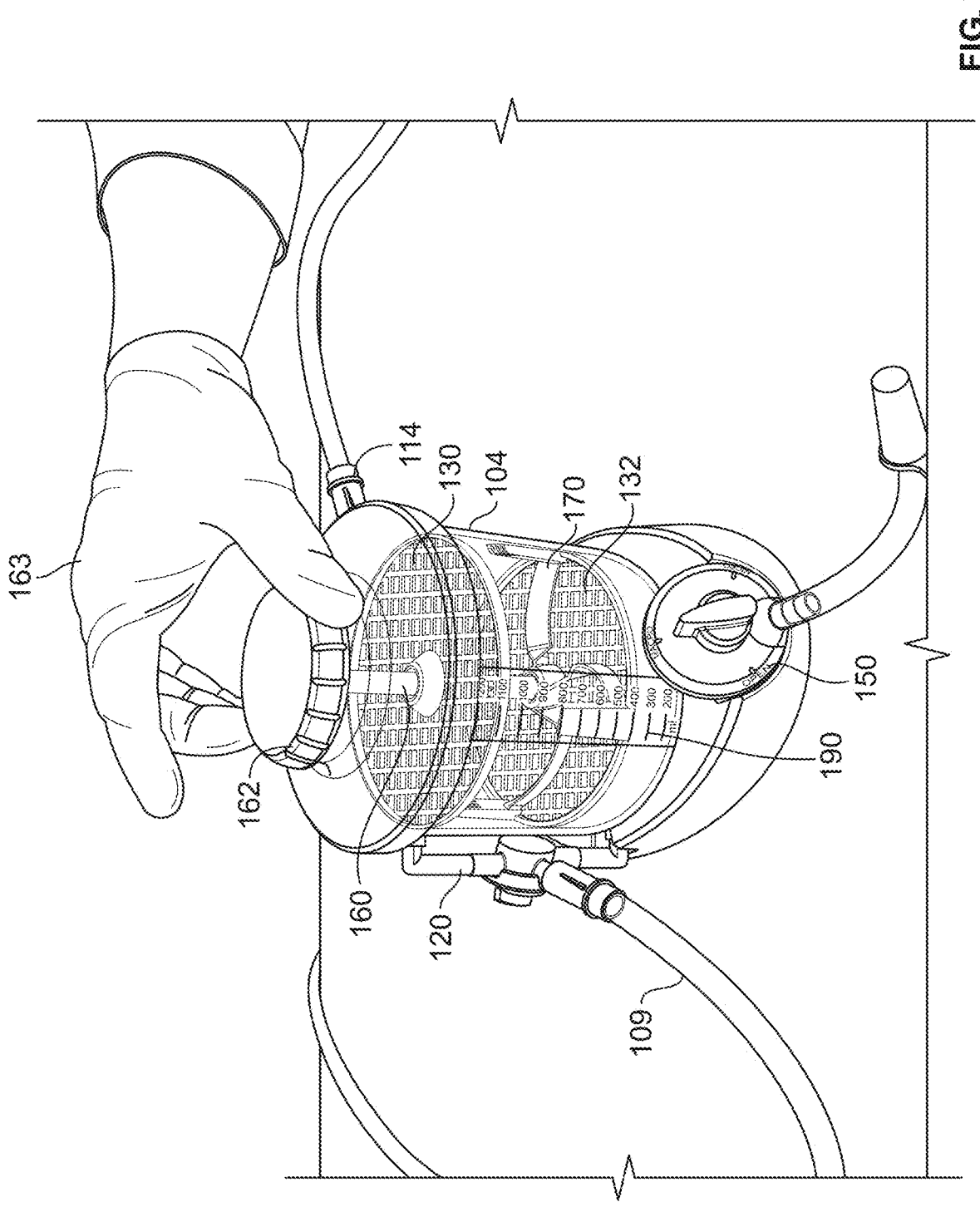
FIG. 7 is a perspective view of the fat harvesting system of FIG. 1 during movement of an actuator, consistent with some embodiments of this disclosure.

Referring to FIGS. 5-7, the second set of blades 170 can be connected to the shaft 164 and disposed above the second screen 132. The second set of blades 170 are connected to the shaft 164 at a hub 176 that is centrally positioned within the second set of blades 170. Each blade 170*a*, 170*b*, 170*c*, 170*d* extends between the hub 176 and an outer ring 178 that surrounds the second set of blades 170. The outer ring 178 can have a diameter that fits within the interior walls 111 of the reservoir body 104. The second set of blades 170 include a blade profile that slopes downwardly to follow the tapered profile of the second screen 132, where the outer ring 178 is positioned at a higher position in the reservoir body 104 than the hub 176. The tapered profile of the second set of blades 170 from a higher position at the interior walls 111 of the reservoir body 104 to a lower position at the hub 176 positioned above the collection chamber 140 facilitates directing the fat cells collected at the second screen 132 into the collection chamber 140 when the second set of blades 170 rotates clockwise (e.g., responsive to clockwise rotation imparted at the actuator 162 by a user 163 illustrated in FIG. 7). Clockwise rotation of the second set of blades 170 causes a leading edge 173 of each blade 170*a-d* to dislodge and direct fat cells captured at the second screen 132 into the collection chamber. Counter-clockwise rotation of the second set of blades 170 causes a trailing edge 175 of each blade 170*a-d* to dislodge and agitate fat cells captured at the second screen 132 within the reservoir body 104.

Each blade 170*a*, 170*b*, 170*c*, 170*d* includes a lateral portion 172, a vertical portion 174, and a hub connector 180. The hub connector 180 and lateral portion 172 of each blade 170*a-d* connect the hub 176 to the outer ring 178. The hub connectors 180 extend from the hub 176 in a first direction that is generally normal to the hub 176 at each hub connector 180 location. The lateral portions 172 have an arcuate profile that extends between the hub connector 180 and the outer ring 178.

The hub connectors 180 extend from the hub 176 at an angle that orients the leading edge 173 at the hub connector 180 downwards or towards the collection chamber 140 (e.g., when the second set of blades 170 are rotated clockwise). In some embodiments, the angle between the hub connector 180 and the hub 176 at the leading edge 173 can be between 0 and 90 degrees, between 10 and 80 degrees, between 20 and 70 degrees, between 30 and 60 degrees, between 40 and 50 degrees, or about 45 degrees. The corresponding trailing edge 175 of each hub connector 180 can be oriented at an upward angle with respect to the hub 176 and away from the collection chamber 140. The upward angle of the hub connector 180 can be the opposing side of the angle between the hub connector 180 and the hub 176 at the leading edge 173.

Still referring to FIGS. 5-7, the lateral portions 172 extend between the hub connector 180 and the outer ring 178. The lateral portions 172 have an arcuate profile (see e.g., side view in FIG. 2, top view in FIG. 5, bottom view in FIG. 6B) that extends between the hub connector 180 and the outer ring 178. The arcuate profile of the lateral portions 172 can create a concave surface along the leading edge 173 of the lateral portions 172 and a convex surface along the trailing edge 175 of the lateral portions 172. The concave surface along the leading edge 173 facilitates the collection of fat cells captured at the second screen 132 and directs the fat cells towards the hub connectors 180 and the collection chamber 140 when the second set of blades 170 are rotated clockwise.

The lateral portions 172 can each include an angled face 177 positioned above the leading edge 173. The angled face 177 can extend at an angle away from the leading edge 173, and the angle of the angled face 177 can extend the angled face 177 in a direction away from the hub connectors 180 along the leading edge 173. For example, the angled face 177 can face at a generally upward angle while the hub connector 180 is oriented generally downwards and towards the collection chamber 140. The upward angle of the angled face 177 can facilitate the collection of fat cells captured at or above the second screen and facilitate the collection and direction of the fat cells towards the hub connectors 180 and the collection chamber 140. In some embodiments, the angled face 177 can facilitate circulation of a wash fluid through the fat cells by pushing the lower layers of fluid up to better mix the stratified layers of the decanted solution and clean the fat cells.

The second set of blades 170 includes vertical portions 174 that extend from the end of each lateral portion 172 and/or the outer ring 178. The vertical portions 174 extend upwardly from the outer ring 178 and along the inner wall 111 of the reservoir body 104. The vertical portions 174 can facilitate the collection of fat cells captured above the second screen 132 (e.g., along the inner walls 111 and above the second screen 132) and facilitate the collection and direction of the fat cells towards the lateral portions 172, the hub connectors 180, and the collection chamber 140. The vertical portions 174 can extend to a height that is between the second screen 132 and the first screen 130. In some embodiments, the vertical portions 174 can extend to a height that does not reach the height of the first screen 130. In some embodiments, the vertical portions 174 can extend to a height that contacts or nearly contacts the first screen 130. The vertical portions 174 can facilitate selective removal of oil from the higher layers of the solution where it collects after decanting to better to better remove the oil.

In some embodiments, the second set of blades 170 facilitates a rapid and effective clearing of the second screen 132 and/or dislodging of material (e.g., fat cells) captured at the second screen 132. The second set of blades 170 can rapidly and effectively dislodge material captured at a bottom of the second screen 132 (e.g., at the transition between the second screen and the collection chamber 140) and/or at a top of the collection chamber 140 to unclog the second screen 132 and/or the collection chamber 140. The second set of blades 170 advantageously facilitates clearing the second screen 132 to permit and/or increase fluid drainage through the second screen 132 and increases the processing speed at which fat cells can be separated from the bodily fluid and extracted from the fat harvesting system 100.

The second set of blades 170 facilitates the gathering and directing of the washed and harvested fat to the collection chamber 140. In some embodiments the second set of blades 170 can direct the washed and harvested fat cells by rotation of the second set of blades 170 (e.g., via a helical shape of the blades 170) that increases the ease of use, speed, and efficiency of extracting the contents into the syringe 110.

Still referring to FIGS. 5-7, the vertical portions 174 can include one or more apertures 181 positioned along an upper area of the vertical portions 174. The one or more apertures 181 can extend through the vertical portion 174 and into a hollow space within the vertical portions 174. The one or more apertures 181 can be a series of drilled lines that extend through the vertical portions 174 along a top surface and an inner-facing surface of each of the vertical portions 174. In some embodiments, each vertical portion 174 can include three apertures 181.

The hollow area within the vertical portions 174 can extend throughout the second set of blades 170. For example, a bottom end of the second set of blades 170 (see e.g., FIG. 6B) can be a hollow area beneath each of the surfaces and features described above. The hollow area underneath the second set of blades 170 can facilitate communication from the second vacuum port 124 through the one or more apertures 181 of the vertical portions 174. The communication between the second vacuum port 124 and the one or more apertures 181 of the vertical portions 174 can apply a portion of the suction from the second vacuum port 124 to each of the one or more apertures 181. The suction at each of the one or more apertures 181 can facilitate a transfer of a portion of the suction from the second vacuum port 124 vertically and into the area between the first screen 130 and the second screen 132.

Referring to FIG. 7, the user 163 can impart a rotational movement to the actuator 162, and the wiper assembly 160 can rotated to direct fat cells into the collection chamber 140. For example, in response to movement (e.g., rotation) of the actuator 162 external to the reservoir body 104, the wiper assembly 160 can rotate. The wiper assembly 160 is free to rotate clockwise and counter-clockwise, and rotation of the actuator 162 imparts rotation to the shaft 164 that transfers the rotation to the first set of blades 166 and the second set of blades 170. In some embodiments, the first set of blades 166 and the first screen 130 both rotate together responsive to rotation of the shaft 164.

The wiper assembly 160 can be rotated to facilitate processing of the bodily fluid, waste fluid, and fat cells within the reservoir body 104. For example, the rotation of the first set of blades 166 and the first screen 130 can agitate large particles captured by the first screen 130 and facilitate movement of the bodily fluid and fat cells through the first screen 130. Rotation of the second set of blades 170 with respect to the second screen 132 can agitate tissues and particles captured at the second screen 132. Clockwise rotation of the second set of blades 170 can guide the fat cells captured at the second screen 132 into the collection chamber 140.

In some embodiments, the reservoir body 104 can include volumetric indications 190 along an outer surface of the reservoir body 104. The volumetric indications 190 can illustrate to a user (e.g., user 163) the volume of fluid and/or fat cells within the reservoir body 104 at a given time during a procedure. The reservoir body 104 can include transparent components to facilitate viewing of the materials contained in the reservoir body 104 so a user can see a volume, color, and consistency of the materials within the reservoir body 104 during operation of the system 100. In some embodiments, touch points of the system 100 can be opaque. For example, the actuator 162, the vacuum knob 126, and the adjustable sizing assembly 150 can be opaque.

Figures 8, 9:
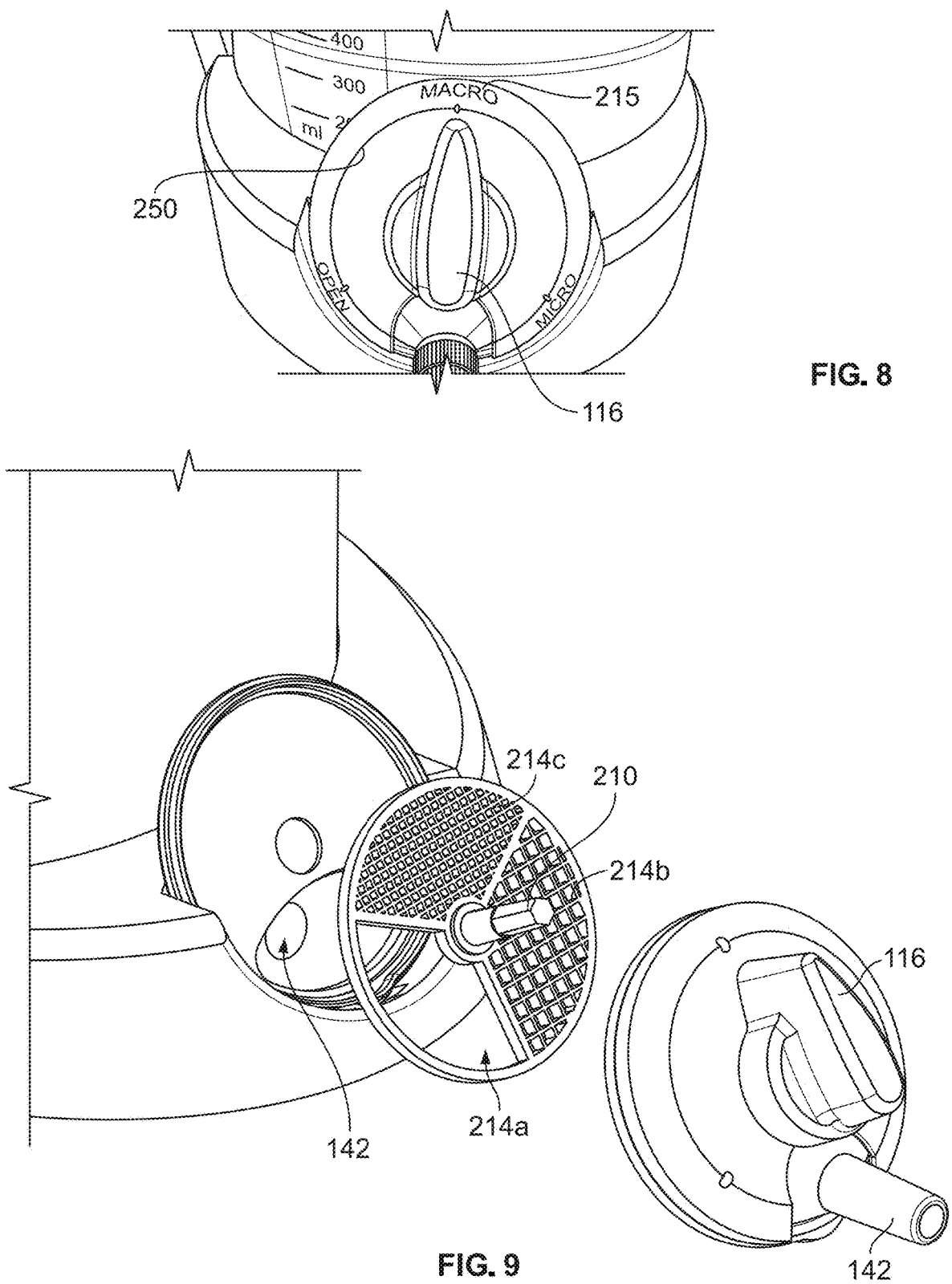
FIG. 8 is a detailed perspective view of a size selector knob, consistent with some embodiments of this disclosure.
FIG. 9 is an exploded perspective view of the size selector knob of FIG. 8.

Referring to FIGS. 8 and 9, the adjustable sizing assembly 150 that is positioned along the extraction conduit 142 can facilitate the positioning of the adjustable sizing screen 152 so that a user can select a size of fat cells for extraction (e.g., by an extraction syringe 110) at an end of the extraction conduit 142. The end of the extraction conduit 142 can be an extension past the adjustable sizing assembly 150 that can be configured to connect to the extraction syringe 110 directly and/or can connect to another conduit or adapter that is configured to connect to the extraction syringe 110.

The adjustable sizing assembly 150 can include an adjustable sizing screen 152, a sizing shaft assembly 210, and a sizing selector 116. The adjustable sizing screen 152 can be a porous screen that includes a flat, disc shaped screen includes a plurality of screen portions, for example, screen portions 214a, 214b, 214c, and each of the screen portions has a different sized pore or screen opening. For example, screen portion 214a can be open and not include a screen or filter within the area of the screen portion 214a, screen portion 214b can have screen openings of 2.4 mm, and screen portion 214c can have screen openings of 1.2 mm. In some embodiments, each of the screen portions 214a, 214b, 214c generally defines a 120° arcuate portion of the adjustable sizing screen 152 when there are three screen portions 214a, 214b, 214c (360°/3 screen portion equals 120° arcuate portion). Similarly, if there were four screen portions, the arcuate portion defined by the screen portions would be 90° and if there were two screen portions, the arcuate portion defined by the screen portions would be 180°.

The sizing shaft assembly 210 can be connected to the sizing selector 116 and the adjustable sizing screen 152 to control the rotational positon of each of the screen portions 214a, 214b, and 214c. The rotational position of the screen portions 214a, 214b, 214c are controlled to select one of the screen portions 214a, 214b, 214c to traverse a cross-sectional portion of the extraction conduit 142. A user can operate the sizing selector between at least three positions The sizing selector 116 can include a sizing indicia 215 on an exterior surface of the sizing selector 116, wherein the sizing indicia 215, including words such as, for example, micro, macro, and open or numbers such as 2.4, 1.2, and open or infinite can be arranged so as to provide a medical professional with an external, visual indication as to where the screen portions 214a, 214b, 214c are arranged across a cross-section of the extraction conduit 142. The adjustable sizing screen 152 can include one or more circumferential seal members positioned around the circumference of the adjustable sizing screen 152 to provide a fluid tight seal around the adjustable sizing screen 152.

Figures 10, 11:
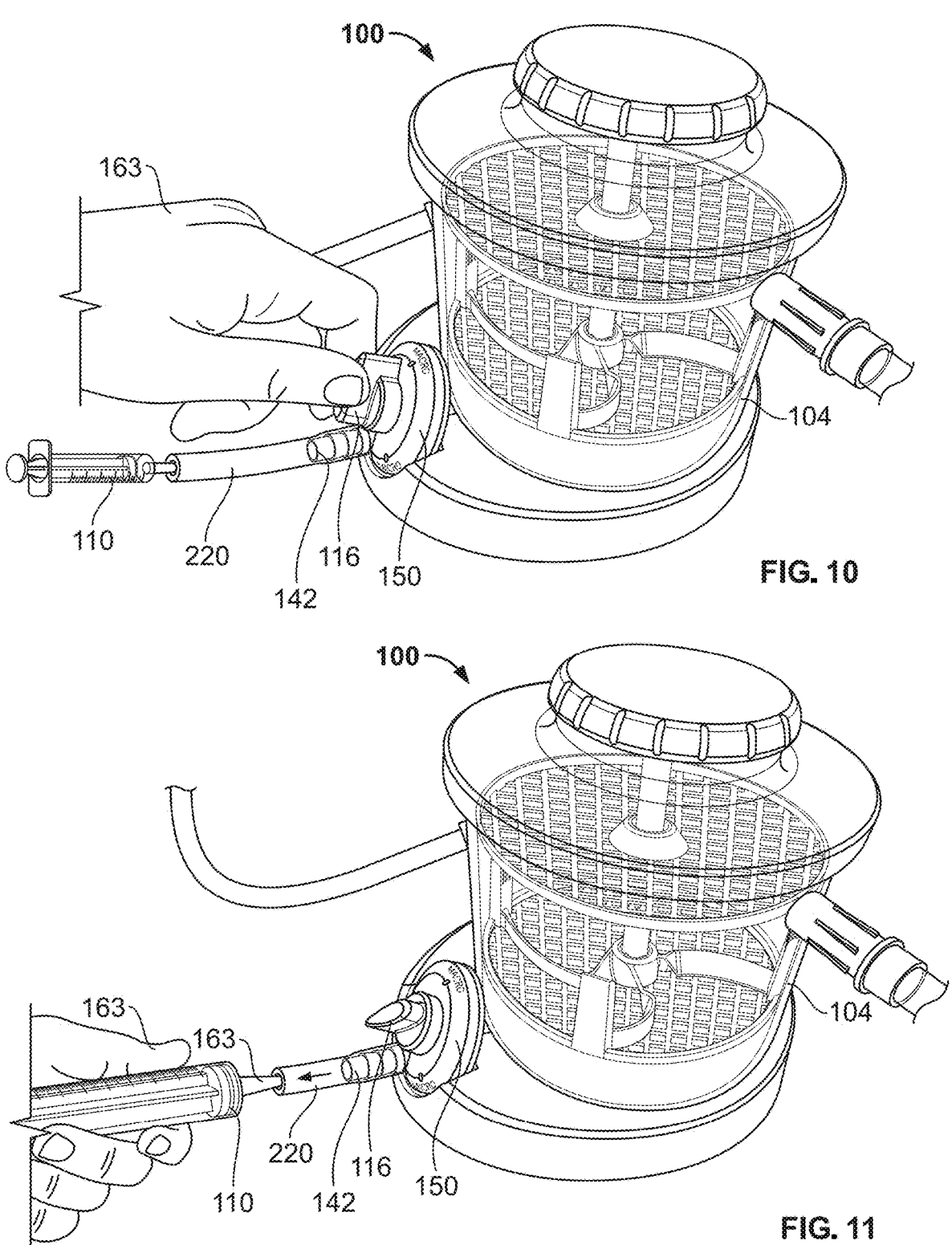
FIG. 10 is a perspective view of the system for fat harvesting of FIG. 1 during operation of the size selector knob.
FIG. 11 is a perspective view of the system for fat harvesting of FIG. 1 during operation of an extraction syringe.

Referring to FIGS. 10 and 11, the user 163 can actuate (e.g., rotate relative to the reservoir body 104) the sizing selector 116 to select one of the screen portions 214a, 214b, 214c for position across the cross-sectional area of the extraction conduit 142. With the sizing selector 116 positioned in a user-selected position, the extraction syringe 110 that releasably mated with a conduit extension 220 of the extraction conduit 142 can extract fat cells. The extraction syringe 110 can be removed after it has been filled, and the extraction syringe 110 can be utilized for transfer/reinjection of the extracted fat cells into another area of a patient. Some embodiments can include one or more extraction syringes 110 that can be implemented to extract various volumes and sizes of fat cells for transfer/reinjection into various body locations.

In some embodiments, if a clog of the adjustable sizing screen 152 occurs, the user can rotate the sizing selector 116 back and forth to wipe the adjustable sizing screen 152. The user can stage the processing of fat cells through the adjustable sizing screen 152 by drawing an amount of fat cells through the adjustable sizing screen 152 and starting with the open setting and pulling an amount of fluid and/or cells (e.g., 10-30 cc) through the device into the syringe 110. The setting of the adjustable sizing screen 152 can be changed to Macro and pushing the contents back through the adjustable sizing screen 152 and into the extraction conduit 142. The user can subsequently change the sizer to Micro and draw the material back into the syringe 110. These steps are a non-limiting example of a user implemented a staged process to provide a more uniform size of fat cells in the extraction syringe 110. The user could also cycle any of the stages repeatedly as they desire.

Figure 12:
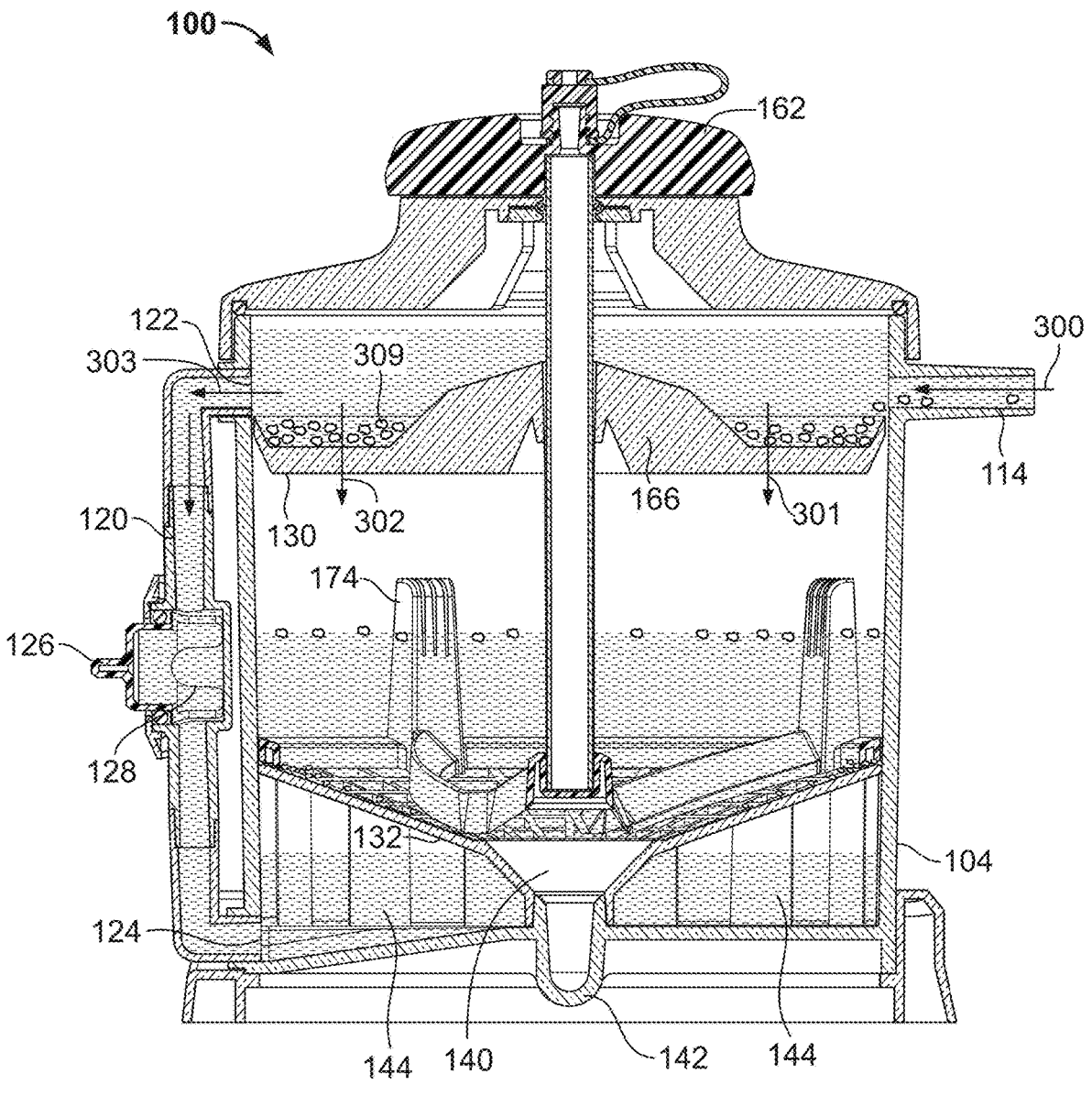
FIG. 12 is a cross sectional view of the fat harvesting system of FIG. 1 along the line 2-2 during operation of the system.

FIGS. 12-14B illustrate example process steps utilizing the system 100. Referring to FIG. 12, some embodiments can include an operating mode where the first vacuum port 122 is on and the second vacuum port 124 is off. At location 300, the bodily fluid including fat cells enters the reservoir body 104 at the input fluid connector 114. The location 300 can be supplied with bodily fluid including fat cells by a liposuction device such as liposuction wand 102. The bodily fluid can fill into the reservoir body 104 and interface with the first screen 130. The first screen 130 can capture larger particles 309 (e.g., fat globules, elongate tissue materials) and permit fat cells and a portion of the bodily fluid to pass through the first screen 130 (see e.g., locations 301, 302). With the first vacuum port 122 in communication with the vacuum source 106, a portion of the bodily fluid is extracted through the first vacuum port 122 and passed to the waste container 108 (see e.g., location 303). In some embodiments, the bodily fluid can pass through location 303 before passing through the first screen 130. The bodily fluid and fat cells that are not captured by the first screen 130 and/or the first vacuum port 122 can flow past the first screen 130. A portion of bodily fluid can pass through the second screen 132 and fill the fluid collection chamber 144 with the second vacuum port 124 not applying suction to the fluid collection chamber 144. A portion of the fat cells can float at a top of the bodily fluid.

Figure 13:
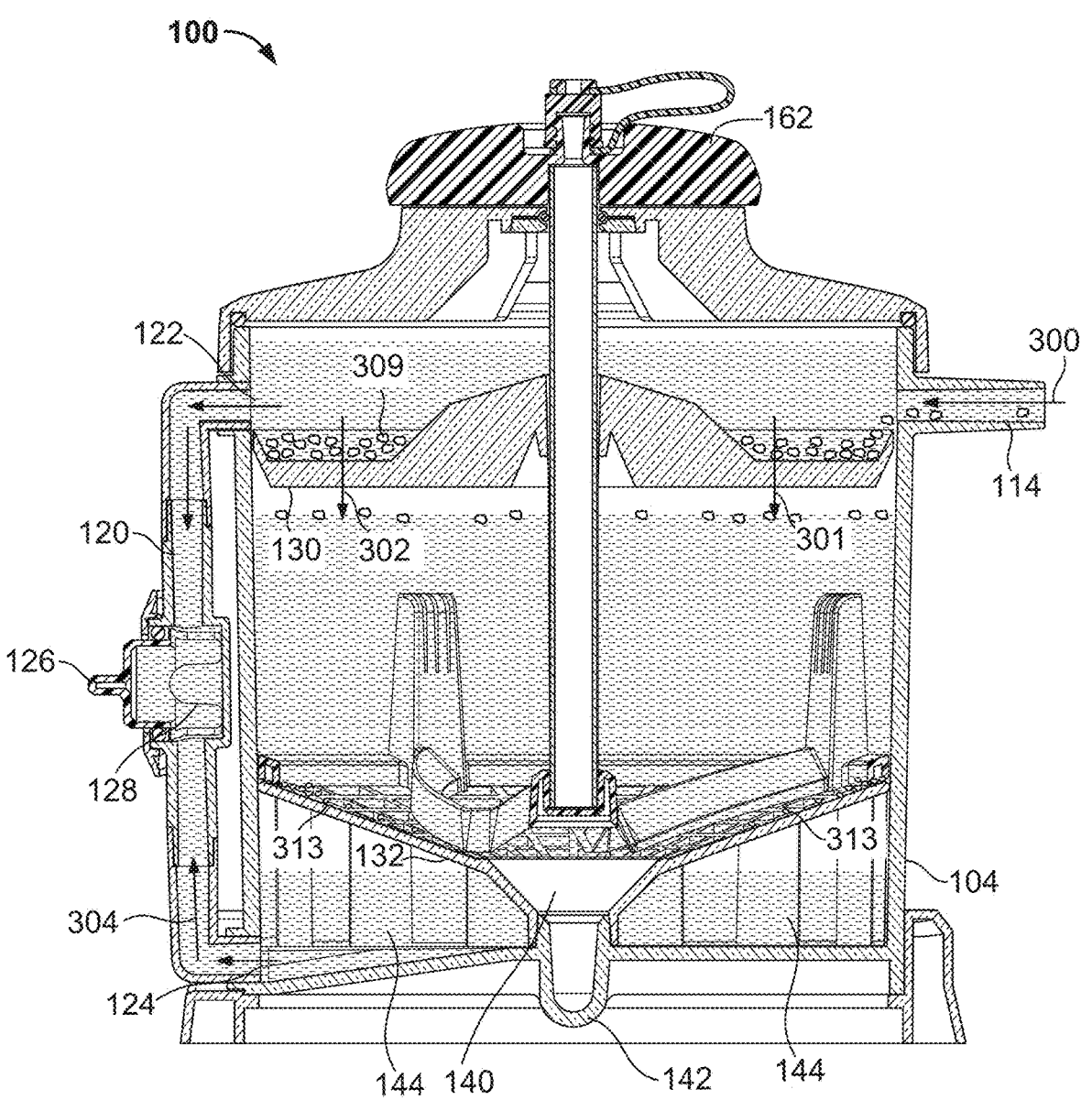
FIG. 13 is a cross sectional view of the fat harvesting system of FIG. 12 at another operation step of the system.

Referring to FIG. 13, some embodiments can include an operating mode where the second vacuum port 124 is on and the first vacuum port 122 is off. Bodily fluid including fat cells can continue to be delivered at location 300. With the first vacuum port 122 turned off, the bodily fluid is not extracted through the first vacuum port 122, and the bodily fluid flows into the reservoir body 104. The bodily fluid and fat cells that are not captured by the first screen 130 can flow past the first screen 130. A portion of bodily fluid can pass through the second screen 132 and fill the fluid collection chamber 144. The second vacuum port 124 can apply suction to the fluid collection chamber 144 to extract fluid from the fluid collection chamber 144 (see e.g., location 304) while additional bodily fluid including fat cells can continue to be delivered at location 300. A portion of the fat cells 313 can be captured by the second screen 132. A portion of the fat cells (e.g., layer of fat cells 310 in FIG. 14A) can float at a top of the bodily fluid (e.g., bodily fluid layer 311 in FIG. 14A).

In some embodiments, the vacuum selector knob can be turned to the off position so that suction is not applied to the reservoir body 104. The off position can be selected with bodily fluid and fat cells in the reservoir body 104 to facilitate a decanting process of the fat cells. For example, the decanting process can include allowing the bodily fluid and the fat cells to remain in the chamber without suctioning off portions of the bodily fluid, thereby allowing separation of the bodily fluid and the fat cells. The decanting process can facilitate a gentle extraction and separation of the fat cells from the bodily fluid and can provide the user with high quality fat cells for use in fat transfer/reinjection. In some embodiments, the decanting process can include the introduction of a washing fluid via the washing fluid introduction path 200. The washing fluid can be introduced after a portion or majority of the bodily fluid has been extracted from the reservoir housing (e.g., via the first vacuum port 122, the second vacuum port 124, or both). The washing fluid and fat cells can be contained in the reservoir housing for an interval of time before extracting fat cells and the washing fluid from the reservoir body 104. The decanting process can optionally include agitation of the suspended solution where the wiper assembly 160 is rotated either clockwise or counter-clockwise to agitate the solution and facilitate additional separation, washing, and/or decanting of the fat cells. The decanting process can advantageously facilitate an atraumatic harvesting of fat cells.

Some embodiments can include an operating mode where the first vacuum port 122 and the second vacuum port 124 are both on and applying suction to the reservoir body 104 via the vacuum source 106. The operating mode with both suction ports on facilities an expedited extraction process that rapidly withdraws and separates the fat cells from the bodily fluid.

Figures 14A, 14B:
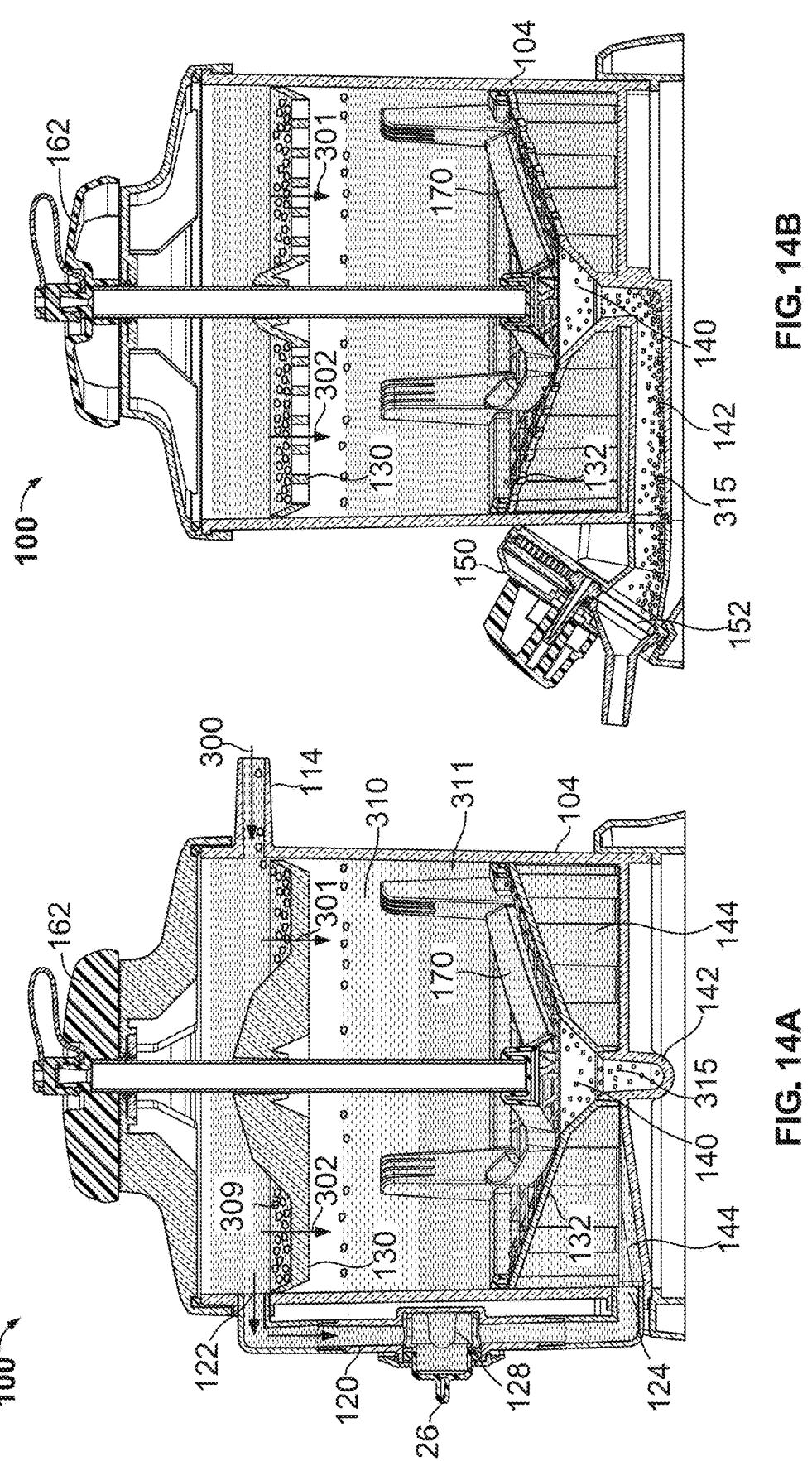
FIG. 14A is a cross sectional view of the fat harvesting system of FIG. 12 at another operation step of the system.
FIG. 14B is a cross sectional view of the fat harvesting system of FIG. 1 along the line 3-3 during the operation step of FIG. 14A.

Referring to FIGS. 14A and 14B, the fat cells (e.g., shown in FIGS. 13, 14A, and 14B as fat cells 315) can be directed from the second screen 132 and collected in the collection chamber 140 and the extraction conduit 142, and the bodily fluid can be separated from the fat cells. For example, the fat cells can be directed into the collection chamber 140 by the tapered profile of the second screen 132 and the second set of blades 170 to collect the fat cells in the collection chamber 140. The fat cells can fill the extraction conduit 142 and can pass through the adjustable sizing assembly 150 and an adjustable sizing screen 152 before being loaded into the extraction syringe.

In some examples, some bodily fluid and/or waste fluid can enter the collection chamber 140 and extraction conduit 142 before the fat cells fill the collection chamber 140. As an optional initial step, a user can extract a volume of waste fluid using an extraction syringe for discarding before a decanting process or washing process occurs in the reservoir body 104. In some embodiments, a user can use a staged-sizing approach to extracting the fat cells. The staged-sizing approach can include extracting a large size (e.g., the open setting of the adjustable sizing screen 152) of fat cells. Subsequently, the user can actuated the selector knob 116 to select a smaller size (e.g., macro or micro). The changing of the size selection knob 116 can be cycled depending on the user selection and preferences.

While this specification contains many specific implementation details, these should not be construed as limitations on the scope of the disclosed technology or of what may be claimed, but rather as descriptions of features that may be specific to particular embodiments of particular disclosed technologies. Certain features that are described in this specification in the context of separate embodiments can also be implemented in combination in a single embodiment in part or in whole. Conversely, various features that are described in the context of a single embodiment can also be implemented in multiple embodiments separately or in any suitable subcombination. Moreover, although features may be described herein as acting in certain combinations and/or initially claimed as such, one or more features from a claimed combination can in some cases be excised from the combination, and the claimed combination may be directed to a subcombination or variation of a subcombination. Similarly, while operations may be described in a particular order, this should not be understood as requiring that such operations be performed in the particular order or in sequential order, or that all operations be performed, to achieve desirable results. Particular embodiments of the subject matter have been described. Other embodiments are within the scope of the following claims.

Accordingly, other implementations are within the scope of the following claims.

What is claimed is:

1. A fat harvesting system, comprising:

a reservoir body having an input fluid connector to receive bodily fluid including fat cells from a liposuction device so that the bodily fluid is deliverable into the reservoir body;

a first screen positioned gravitationally below the input fluid connector and extending across the reservoir body, the first screen having a first screen size;

a second screen positioned gravitationally below the first screen, the second screen having a tapered profile that slopes downwardly from an inner wall of the reservoir body to a collection chamber positioned along a midline of the reservoir body, the second screen having a second screen size that is smaller than the first screen size;

a vacuum control housing that includes a first vacuum port in communication with the reservoir body above the first screen and a second vacuum port in communication with the reservoir body below the second screen, the first vacuum port and the second vacuum ports are positioned to remove a separated aqueous layer of the bodily fluid while a harvested fat layer including the fat cells remains in the reservoir body;

a wiper rotatably mounted within the reservoir body so as to rotate about an axis of the reservoir body in response to movement of an actuator external to the reservoir body, the wiper having a set of blades disposed above the second screen;

a conduit that extends from the collection chamber and is configured to connect to an extraction syringe to withdraw at least a portion of the fat cells from the collection chamber of the reservoir body; and an adjustable sizing screen positioned along the conduit and having a plurality of arcuate screen portions that are movable relative to the reservoir body so that said portion of the fat cells advance through a selected one of the arcuate screen portions before reaching the extraction syringe.

2. The fat harvesting system of claim 1, wherein the vacuum control housing includes a vacuum selector knob that is rotatable relative to the vacuum control housing, the vacuum selector knob is connected to a vacuum control housing valve that controls fluid communication through the vacuum control housing.

3. The fat harvesting system of claim 2, wherein the vacuum selector knob is rotatable to control the vacuum control housing valve to selectively provide fluid communication between the first vacuum port and a vacuum source, the second vacuum port and the vacuum source, both the first and second vacuum ports and the vacuum source, or neither vacuum port and the vacuum source.

4. The fat harvesting system of claim 1, comprising a fluid collection chamber gravitationally below the second screen, the fluid collection chamber is separated from the collection chamber.

5. The fat harvesting system of claim 4, wherein the second vacuum port is in fluid communication with the fluid collection chamber.

6. The fat harvesting system of claim 1, wherein bodily fluid and fat cells can pass through the first screen and fat cells are prevented from passing through the second screen.

7. The fat harvesting system of claim 1, the second screen comprising a porous screen cover that prevents fat cells from passing through the second screen and permits bodily fluids to pass through the second screen.

8. The fat harvesting system of claim 1, wherein the set of blades have a blade profile that slopes downwardly to follow the tapered profile of the second screen, wherein the set of blades includes a plurality of lateral portions that follow the tapered profile of the second screen and a plurality of vertical portions that extend vertically from the respective lateral ends of the plurality of lateral portions along the inner wall of the reservoir body.

9. The fat harvesting system of claim 8, wherein responsive to movement of an actuator external to the reservoir body, the set of blades rotates to direct fat cells into the collection chamber.

10. The fat harvesting system of claim 1, wherein a first arcuate screen portion of the plurality of arcuate screen portions of the adjustable sizing screen has a first screen opening size, and a second arcuate screen portion of the plurality of arcuate screen portions of the adjustable sizing screen has a second screen opening size that is smaller than the first screen opening size, wherein the fat harvesting system further comprises a size selector knob that is rotatable relative to the reservoir body so that the selected one of the arcuate screen portions is positioned to contact said portion of the fat cells.

11. The fat harvesting system of claim 1, wherein the adjustable sizing screen has a circular periphery and each arcuate screen portion is a 120-degree arcuate portion of the adjustable sizing screen.

12. The fat harvesting system of claim 1, further comprising a wash introduction path in communication with the reservoir body to receive a wash fluid into the body reservoir so that the wash fluid contacts the harvested fat layer including the fat cells.

13. The fat harvesting system of claim 1, wherein a distal tip of the extraction syringe is releasable from the conduit so that said portion of the fat cells are transferable to a reinjection site.

14. The fat harvesting system of claim 13, further comprising an additional extraction syringe that is releasably matable to the conduit to withdraw a second portion of the fat cells from the collection chamber of the reservoir body.

15. The fat harvesting system of claim 1, wherein the first screen and the wiper are removable from the reservoir housing.

16. The fat harvesting system of claim 1, wherein the system is a harvested fat protected system.

17. A fat harvesting method comprising:

receiving bodily fluid including fat cells in a reservoir body from a liposuction device;

screening the bodily fluid by a first screen extending across the reservoir body, the first screen having a first screen size;

removing a portion of a waste fluid from the bodily fluid and the reservoir body by a first vacuum port positioned gravitationally above the first screen;

capturing fat cells at a second screen gravitationally below the first screen, the second screen having a second screen size that is smaller than the first screen size;

removing a second portion of a waste fluid from the bodily fluid and the reservoir body by a second vacuum port positioned gravitationally below the second screen;

collecting fat cells in a collection chamber gravitationally below the second screen; and extracting fat cells through a selected screen portion of an adjustable sizing screen having a plurality of adjacent screen portions that are movable relative to the reservoir body and into an extraction syringe.

18. The method of claim 17 further comprising rotating a set of blades positioned above the second screen to direct fat cells captured by the second screen towards a collection chamber.

19. The method of claim 17, further comprising:

introducing a wash fluid into the reservoir body;

decanting the fat cells in the wash fluid for an interval of time;

extracting the wash fluid; and extracting the fat cells into the extraction syringe.

20. The method of claim 17, wherein the first vacuum port and the second vacuum port are independently operable and operable together.

\* \* \* \* \*